United States Patent
Expósito Tarrés et al.

(10) Patent No.: US 12,285,513 B2
(45) Date of Patent: Apr. 29, 2025

(54) CELL-FREE PLANT CELL CULTURE SUSPENSION SUPERNATANT WITH RE-YOUTH ACTIVITY AND/OR WOUND HEALING ACTIVITY OVER SKIN CELLS

(71) Applicant: VYTRUS BIOTECH, S.L., Terrassa (ES)

(72) Inventors: Òscar Expósito Tarrés, Terrassa (ES); Albert Jané Font, Terrassa (ES); Sara Laplana Lasierra, Terrassa (ES); Maria Mas Duarte, Terrassa (ES); Tarik Ruiz Medina, Terrassa (ES); Jessica Romero Rueda, Ripollet (ES)

(73) Assignee: VYTRUS BIOTECH, S.L., Terrassa (ES)

( * ) Notice: Subject to any disclaimer, the term of this patent is extended or adjusted under 35 U.S.C. 154(b) by 699 days.

(21) Appl. No.: 15/566,601

(22) PCT Filed: Apr. 11, 2016

(86) PCT No.: PCT/EP2016/057885
§ 371 (c)(1),
(2) Date: Oct. 13, 2017

(87) PCT Pub. No.: WO2016/166047
PCT Pub. Date: Oct. 20, 2016

(65) Prior Publication Data
US 2018/0133138 A1    May 17, 2018

(30) Foreign Application Priority Data
Apr. 14, 2015 (EP) .................................. 15163515

(51) Int. Cl.
| | | |
|---|---|---|
| A61K 8/64 | (2006.01) | |
| A61K 8/34 | (2006.01) | |
| A61K 8/9789 | (2017.01) | |
| A61K 8/9794 | (2017.01) | |
| A61K 36/185 | (2006.01) | |
| A61K 36/23 | (2006.01) | |
| A61K 38/16 | (2006.01) | |
| A61K 47/10 | (2017.01) | |
| A61P 17/00 | (2006.01) | |
| A61P 17/02 | (2006.01) | |
| A61Q 19/00 | (2006.01) | |
| A61Q 19/02 | (2006.01) | |
| A61Q 19/08 | (2006.01) | |

(52) U.S. Cl.
CPC ............. *A61K 8/645* (2013.01); *A61K 8/345* (2013.01); *A61K 8/64* (2013.01); *A61K 8/9789* (2017.08); *A61K 8/9794* (2017.08); *A61K 36/185* (2013.01); *A61K 36/23* (2013.01); *A61K 38/168* (2013.01); *A61K 47/10* (2013.01); *A61P 17/00* (2018.01); *A61P 17/02* (2018.01); *A61Q 19/00* (2013.01); *A61Q 19/02* (2013.01); *A61Q 19/08* (2013.01)

(58) Field of Classification Search
CPC ........................................................ A61K 36/00
USPC ............................................................ 424/725
See application file for complete search history.

(56) References Cited

U.S. PATENT DOCUMENTS

| | | |
|---|---|---|
| 4,139,619 A | 2/1979 | Chidsey, III |
| 4,596,812 A | 6/1986 | Charles, III et al. |
| 6,281,241 B1 | 8/2001 | Elsner |
| 2014/0072619 A1 | 3/2014 | Blum et al. |
| 2015/0359830 A1 | 12/2015 | Stottlemyre et al. |

FOREIGN PATENT DOCUMENTS

| | | | |
|---|---|---|---|
| CN | 103976908 A | | 8/2014 |
| DE | 19817177 | * | 10/1999 |
| DE | 19817177 A1 | | 10/1999 |
| EP | 1243654 A1 | | 9/2002 |
| EP | 1498475 A1 | | 1/2005 |
| EP | 2436759 A2 | | 4/2012 |
| EP | 2687592 A1 | | 1/2014 |
| EP | 2708596 A1 | | 3/2014 |
| FR | 2854328 B1 | | 8/2006 |
| WO | WO 2006/087759 A2 | | 8/2006 |
| WO | WO 2007/113851 A2 | | 10/2007 |
| WO | WO 2012/017067 A1 | | 2/2012 |
| WO | WO 2012/130783 A2 | | 10/2012 |
| WO | WO 2016/166047 A1 | | 10/2016 |

OTHER PUBLICATIONS

International Search Report and Written Opinion mailed Jul. 21, 2016 for PCT/EP2016/057885, 14 pages.
Choi, Jae-Hoon, et al: Antitumor activity of cell suspension culture of green tea seed (*Camellia sinensis* L.), Biotechnology and Bioprocess Engineering, Sep. 1, 2006, vol. 11, pp. 396-401.
Czyzewicz, Nathan, et al: "Message in a bottle: small signalling peptide outputs during growth and development", Journal of Experimental Botany, Sep. 7, 2013, vol. 654, No. 17, pp. 5281-5296.
Dimri, Goberdhan P., et al: "A biomarker that identifies senescent human cells in culture and in aging skin in vivo", Proc. Natl. Acad. Sci. USA, Sep. 1995, vol. 92, pp. 9363-9367.

(Continued)

*Primary Examiner* — Michael V Meller
(74) *Attorney, Agent, or Firm* — Squire Patton Boggs (US) LLP

(57) ABSTRACT

The invention relates to cell-free supernatants (conditioned media) that previously supported the growth of a dedifferentiated plant cell suspension culture, or a fraction of said cell-free supernatant, said cell-free supernatant or said fraction comprising peptides from 4 to 300 amino acids length and including peptide plant growth factors and peptide plant transcription factors, and without having cytoplasmic cell contents from the cell lysis and membranes and/or cell walls. The invention also relates to fractions of said supernatants and to cosmetic applications for promoting re-youth of skin.

6 Claims, 10 Drawing Sheets
Specification includes a Sequence Listing.

(56) References Cited

OTHER PUBLICATIONS

Matsubayashi, Yoshikatsu, et al: "Phytosulfokine, sulphated peptides that induce the proliferation of single mesophyll cells of *Asparagus officinalis* L.", Proc. Natl. Acad. Sci. USA, Jul. 1996, vol. 93, pp. 7623-7627.
Ryan, Clarence A., et al: "Polypeptide Hormones", The Plant Cell Supplement May 2002, pp. S251-S264.
DermaScope: https://www.dermascope.com/ingredients/mineral-skin-care; May 2011, pp. 1-14.
Hellwig, et al. "Plant cell cultures for the production of recombinant proteins", Nature Biotechnology, Gale Group Inc, 2004, vol. 22, No. 11, pp. 1414-1420, Nov. 2004.
Merrell, "The importance of minerals in the long term health of humans", Jost Chemical Co.; Feb. 26, 2016.
Park, "Role of micronutrients in skin health and function", Biomol Ther (Seoul); May 2015; vol. 23(3), pp. 207-217.
Pumthong, et al. "Curcuma aeruginosa, a novel botanically derived 5α-reductase inhibitor in the treatment of male-pattern baldness: a multicenter, randomized, double-blind, placebo-controlled study", Journal of Dermatological Treatment. 2012; vol. No. 23, pp. 385-392, Jul. 2011.
SK Bioland: https://www.skibioland.com/en/raw/makeup_0202.jsp; Oct. 27, 2015. (On Order/USPTO Ticket #1-819053159).
Vitamins in Cosmetics, Medical Beauty Forum 2011; pp. 14-16.

\* cited by examiner (A)

(B)

(C)
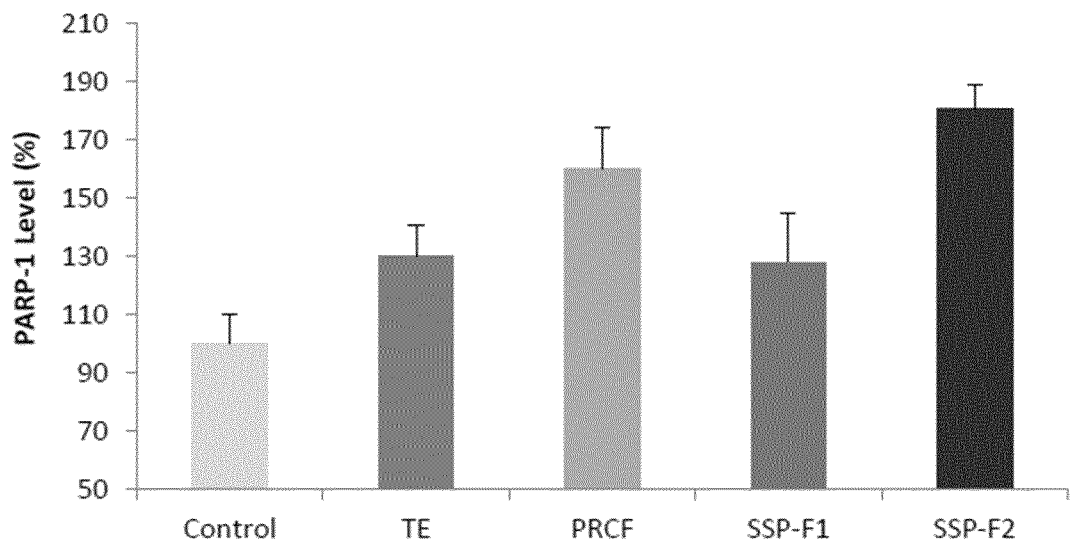
(D)
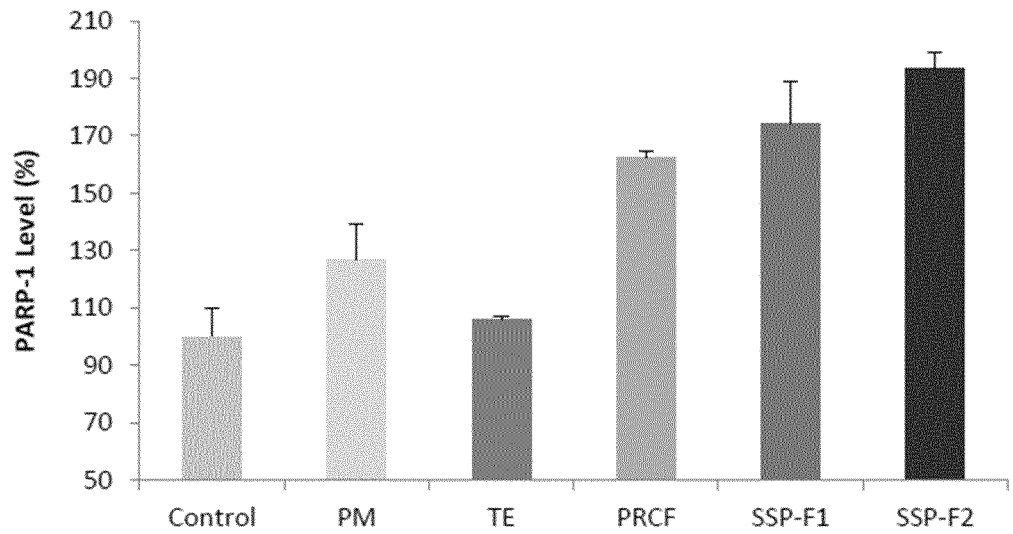
Cont. FIG. 3

(A)

(B)

(A)

(B)

(A)

(B)

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial
<220> FEATURE:
<223> OTHER INFORMATION: Synthetic peptide derived from phytosulfokine-
      beta
<220> FEATURE:
<221> NAME/KEY: ACETYLATION
<222> LOCATION: (1)..(1)
<223> OTHER INFORMATION: Acetylated N-terminal tyrosine
<220> FEATURE:
<221> NAME/KEY: AMIDATION
<222> LOCATION: (4)..(4)
<223> OTHER INFORMATION: Amidation of C-terminal threonine

<400> SEQUENCE: 1

Tyr Ile Tyr Thr
1

<210> SEQ ID NO 2
<211> LENGTH: 4
<212> TYPE: PRT
<213> ORGANISM: Artificial
<220> FEATURE:
<223> OTHER INFORMATION: Synthetic peptide derived from phytosulfokine-
      beta
<220> FEATURE:
<221> NAME/KEY: SULFATATION
<222> LOCATION: (1)..(1)
<223> OTHER INFORMATION: X is a sulphated Tyrosine (Y)
<220> FEATURE:
<221> NAME/KEY: ACETYLATION
<222> LOCATION: (1)..(1)
<223> OTHER INFORMATION: Acetylated N-terminal Tyrosine
<220> FEATURE:
<221> NAME/KEY: AMIDATION
<222> LOCATION: (4)..(4)
<223> OTHER INFORMATION: Amidated C-terminal Threonine

<400> SEQUENCE: 2

Xaa Ile Tyr Thr
1

<210> SEQ ID NO 3
<211> LENGTH: 4
<212> TYPE: PRT
<213> ORGANISM: Artificial
<220> FEATURE:
<223> OTHER INFORMATION: Synthetic peptide derived from phytosulfokine-
      beta
<220> FEATURE:
<221> NAME/KEY: ACETYLATION
<222> LOCATION: (1)..(1)
<223> OTHER INFORMATION: Acetylated N-terminal Tyrosine
<220> FEATURE:
<221> NAME/KEY: SULFATATION
<222> LOCATION: (3)..(3)
<223> OTHER INFORMATION: X is a sulphated Tyrosine (Y)
<220> FEATURE:
<221> NAME/KEY: AMIDATION
<222> LOCATION: (4)..(4)
<223> OTHER INFORMATION: Amidated C-terminal Threonine

<400> SEQUENCE: 3

Tyr Ile Xaa Thr
1
```

CELL-FREE PLANT CELL CULTURE SUSPENSION SUPERNATANT WITH RE-YOUTH ACTIVITY AND/OR WOUND HEALING ACTIVITY OVER SKIN CELLS

The invention relates to compositions derived from plant cell culture suspensions conditioned media, and to methods for obtaining these media that are used in topical pharmaceutical and cosmetic compositions, more particularly topical compositions for facing senescence processes of skin, and/or for skin wound healing.

BACKGROUND ART

Plant extracts have been widely used in pharmacy and cosmetics for the preparation of compositions useful due to the active components derivable from them. Extraction processes with particular solvents or mixtures have been standardized, but they are expensive processes, and allow obtaining only a particular fraction of the compounds in the plants (those that are compatible, miscible with the solvents used in the extraction processes). Besides, extraction from plants means that the plant is available, and although some compounds can be extracted even from the dried stored plants or parts of the plant, in other occasions the fresh plant is needed to assure obtaining the desired or aimed compound or group of compounds if they are only present or in the adequate form in fresh material. Therefore, plant extracts or parts of plants for use in cosmetics imply, among others, the disadvantages of season restrictions, protection of species, limited store capacities, cultivation problems, and non-homogeneity of types due to different suppliers from different origins.

For this reason, current topics in cosmetic and pharmacy using plant compounds relate to the use of plant cell cultures for producing compounds of interest. Plant cell cultures allow the isolation of cells from different parts of the plant (leaves, fruits, stem, roots, shoots, etc.), which isolated plant cells are submitted to cell dedifferentiation until totipotency is reached. These dedifferentiated totipotent cells can be stimulated or submitted to particular stress conditions to make cells produce a compound or compounds of interest. Working with plant cell cultures technology implies the advantage of standardized continuous production of the compounds of interest, independently of seasons and of suppliers.

There are many documents disclosing the use of plant cell culture suspensions or extracts thereof (usually derived from the lysis of the plant cells in suspension). Examples of these include the US2014072619 that discloses cosmetic dermatological compositions comprising a cell lysate of Uttwiler Spaetlauber (an apple variety originated in Switzerland) in the whole culture medium broth encapsulated in liposomes, and which is useful for promoting proliferation, protection and vitalization of skin stem cells, as well as to protect hair follicle.

Likewise, WO2012130783 discloses a cosmetic composition comprising the water soluble conditioned media and the water soluble compound of the inner of the cells of *Oryza sativa*. This composition, when applied topically to human skin cells can modulate DNA gene promoter methylation in young and more particularly intrinsically and extrinsically aged mammalian skin cells, thus being suitable for pushing skin to a younger and healthier state.

The document EP2436759 discloses innately undifferentiated stem cells derived from the cambium of a Solanaceace plant without going through dedifferentiation. These stem cells and the conditioned media that previously supported the growing of the cells are proposed as anti-agent active principles in cosmetic compositions. The authors propose using stem cells derived/isolated from the cambium to avoid the possible serious changes occurring in chromosomes during dedifferentiation processes. Interesting results are shown with a DMSO extract of the stem cells after removing of the culture medium on a model of stressed human fibroblasts. On the other side, results with a dilution of 10% of the culture medium are also shown, although they aren't sufficiently disclosed, since solvent for this 10% dilution of the medium is no mentioned. Therefore, the interesting results could be the consequence the provision of nutrients from the supposed DMEM medium used for diluting de culture media from the stem cells and that is used for growing fibroblasts.

Albeit interesting, obtaining of cell culture suspension lysates (i.e., the cell fraction from the culture re-suspended in a different media and further homogenized for disrupting cells), as well as of extracts of these cells, allow only the recovery of some of the compounds present in the cells and not the whole plant cell cocktail compounds. These compositions show real effects on collagen and pro-collagen synthesis, and they are useful as anti-wrinkle skin treatments, as cicatrizing agents and/or as skin wound healing agents, for example.

On the other hand and providing some benefits, the cell lysates sustained in the media where cells were previously grown, or cells lysates previously isolated from the media, would imply fine adjusting of doses to avoid toxicities due to proteins and other ingredients from the inner of the cells.

For all these reasons, there is thus a need of alternative compositions and compounds derived from plant cell cultures, obtainable in an easy and rentable way and that could be used in cosmetics or pharmacy in the same way that the plant cell culture lysates, or in more particular cosmetic or therapeutically indications.

SUMMARY OF THE INVENTION

The inventors tested and proved that the cell-free supernatants resulting from removal of entire cells in a plant dedifferentiated cell culture suspension really contain cocktails of compounds, acting synergistically together with other extracellular products comprised in the supernatant that supported the growth of these plant cells. These cell-free supernatants surprisingly serve for the purpose of regenerating damaged or old animal cells, in particular mammal dermis (fibroblast), and epidermis (keratinocytes) cells. In addition, several fractions of these supernatants are enriched with the so-called peptide plant growth factors, generally acting in plants as signalling compounds between cells (see below) and also named small signalling polypeptides involved in plant defence, growth and development.

These peptide fractions of the cell-free supernatants produce even a higher effect than the cell-free supernatant and the peptides itself. In addition, and as disclosed herewith, the method of obtaining the cell-free supernatants as well as any fraction thereof is environmentally friendly, easy and non-expensive in comparison with chemical synthesis. Is also to be noted that most of these peptide plant growth factors are not recovered with the extraction processes usually performed directly on plants or parts of plants. Since these peptide plant growth factors are generally extracellular compounds, due to its inherent signalling function, they are present outside the cells more than inside, and thus they cannot be recovered from extracting processes even on cell culture lysates, said lysates obtainable by separating the cells from the culture and then lysing while extracting with a particular solvent.

Thus, in a first aspect the invention relates to cell-free supernatants that previously supported the growth of a dedifferentiated plant cell suspension culture, or a fraction of said cell-free supernatants, for use as a medicament for skin treatment, wherein said cell-free supernatant or said fraction comprises peptides from 4 to 300 amino acids length, said peptides selected from peptide plant growth factors, plant transcription factors and mixtures thereof, and said cell-free supernatants or fraction without having cytoplasmic cell contents from the cell lysis and without having membranes and/or cell walls. They are for use as skin animal cells repairing and/or regenerating agents.

Invention thus provides a medicament for topical use onto the skin, being therefore the cell-free supernatants that previously supported the growth of a dedifferentiated plant cell suspension culture, or a fraction of said cell-free supernatants for topical (medical or cosmetic) use at skin.

Since dedifferentiated plant cells in a suspension culture are those cells that in the real life of the plant would appear in case of wound or of tissue damaged (callus), they synthesise the so-called small signalling polypeptides involved in plant defence, growth and development (see. Ryan et al., "Polypeptide Hormones", *The Plant Cell*—2002, S251-S264 Supplement). These peptides seem to act as extracellular signalling agents to promote the proper communication network between cells in order to promote differentiation or cell proliferation. In other words, plant compounds (peptides) involved in regeneration of the plant and in cicatrisation of damaged plant tissues. The supernatants of the invention or any fraction thereof comprise, in particular, these so-called plant growth factors of peptide nature (as analogy to animal peptide growth factors, such as VEGF, PDGF, EGF, etc.).

In particular, cell-free supernatants that previously supported the growth of a dedifferentiated plant cell suspension culture, or a fraction of said cell-free supernatants, are for use in the regeneration of dermis and epidermis cells. More particularly, they are for use in the regeneration of senescent fibroblasts of the dermis skin layer. For senescent fibroblasts is to be understood those with a phenotype defined by at least one of the following parameters: cell expression of β-Galactosidase (measured as a staining by enzymatic reaction with 5-bromo-4-chloro-3-indolyl β-Galactoside; X-Gal), morphologic alterations (round-shaped cells rather than scattered measured by means of microscopic visualisation, replicative index measured by means of microscopic visualisation, and reactive oxygen species production. For in vitro analysis, a senescent fibroblast is considered one which proceeds from at least 20 passes in the culture.

The use of β-Galactosidase as marker for senescence in human fibroblasts (replicative senescence) is widely detailed in the document of Goberdhan et al., "A biomarker that identifies senescent human cells in culture and in aging skin in vivo", *Proc.Natl.Acad.Sci*—1995, Vol No. 92, pp.: 9363-9367.

Therefore, the cell-free supernatants or fractions thereof containing the peptide plant growth factors and/or plant transcription factors are for use as skin repairing and/or regenerating agents by means of reverting senescence in skin cells (i.e fibroblasts). This ability of reverting senescent phenotype in skin cells (i.e in fibroblasts) makes the cell-free supernatant or any fraction with the peptides from 4 to 300 amino acids length useful in the treatment of old animal skin, in particular old human skin, which usually presents deep wrinkles and expression lines. It makes it also usable in the treatment and/or prophylaxis of premature skin aging. Premature skin aging (also known generically as photoaging) is a particular photoaging defined by a skin appearance comprising wrinkles, altered pigmentation, and loss of skin tone in a premature age, namely in humans 20-50 years old. Photoaged skin displays prominent alterations in the collagenous extracellular matrix of connective tissue and elevated expression of metalloproteinase 1 (MMP1), the enzyme responsible of degrading collagen types I, II and III. Premature skin aging is a multifactorial process, but besides genetic predisposition, environmental factors including accumulated UV and IR radiation, toxic consumption (smoking) and stress have been proved as real causes of this disorder.

As will be depicted in the examples below, the cell-free supernatants or fractions thereof containing the peptide plant growth factors and/or plant transcription factors (at least those peptides from 4 to 300 amino acids length) are effective in the treatment of all the conditions listed above even where other prior art compositions are no longer effective, which means that symptoms associated to these conditions are not ameliorated with these prior art compositions and they are with the cell-free supernatants or fractions thereof of the invention.

"Reverting senescence" means, in the sense of the present invention the promotion in cells of markers or of functions proper of young cells. That is, in particular the promotion of a pattern of expression or repression of genes leading to proteins associated to healthy and young cells. Examples of markers (enzymes, transcription factors, chromatin domains, nuclear proteins and proteins of the basal membrane in epidermis cells) that allow the skilled man to classify a cell as senescent or as young include, as non-limiting examples, Ki67 protein, p21 (CDKN1A) protein, histone γH2AX, Senescence-associated heterochromatin foci (SAHF), the enzyme Senescence-associated beta-galactosidase (Sen-β-Gal), DNA-repairing proteins Ku70 and Ku80, the nuclear protein PARP (Poly-ADP ribose polymerase), Peroxiredoxin 4 (Prx IV, or PRX4) enzyme, the structural proteins Integrin β1, Intregrin β4, laminin B3/5, Keratin 15, the enzymes Quinone reductase and gluthation-s-transferase, and the cell stress markers heat shock proteins and S-proteosome.

According to the inventors' knowledge, this is the first time a plant cell-free supernatant or a fraction thereof with the peptide plant growth factors and/or plant transcription factors has been used over animal skin cells with proved effects on a model of old skin. Therefore, the invention supposes a way to easily recover such active ingredients commonly used by the plants in their tissue regeneration or differentiation processes, with the final aim of having compositions comprising them and that can be safely and effectively applied on animal skin cells.

These supernatants without the inner content of cell cytoplasm and without the cell membranes and/or walls are herewith termed conditioned nutrient media or conditioned media, or conditioned cell-medium. The inventors propose that they resemble the plasma or serum obtained when blood is centrifuged and blood cells (erythrocytes, monocytes, and platelets) are collected at the bottom of the centrifuge recipients and the liquid supernatant (plasma, serum) is collected at the top. The cell-free supernatants of the invention contain thus, not only amounts of those compounds initially present in the culture media where dedifferentiated plant cells were grown and that were not consumed, but also other compounds that dedifferentiated plant cells released to the media. It is thus proposed the use of these conditioned media without the dedifferentiated cells, or of a fraction thereof comprising these peptide plant growth factors and/or transcription factors for promoting regeneration of animal cells, in particular of dermis and/or epidermis cells of mammals, and more particularly humans.

The fractions of said cell-free supernatants, the fractions comprising peptides from 4 to 300 amino acids length, being plant growth factors or plant transcription factors, or plant epigenetic factors can also be defined as "isolated" compositions (or isolated fractions) comprising peptides from 4 to 300 amino acids length and obtainable from the cell-free supernatant that previously supported the growth of a dedifferentiated plant cell suspension culture. In particular, isolation of such compositions comprise separating or recovering a liquid from the said supernatant with the peptide plant growth factors by means of at least a protein separation process, said process comprising at least one of chromatography (selected from solid-phase extraction (SPE), size-exclusion chromatography (SEC), and combination in cascade thereof), filtering (in particular by tangential flow filtration (TFF)), protein precipitation, and combinations thereof. These compositions comprising peptide plant growth factors and/or plant transcription factors and/or epigenetic factors so obtained are, in particular, for use as skin animal cells repairing and/or regenerating agents as above exposed.

The invention provides also particular new fractions of these cell free-supernatants derived or obtained from plant cell suspension cultures of particular plant species, and that have the effect disclosed above.

The invention has therefore as a second aspect a fraction of a cell free-supernatant, which previously supported the growth of a dedifferentiated plant cell suspension culture, from a plant selected from the group consisting of *Daucus carota, Centella asiatica, Punica granatum, Gossypium herbaceum, Sarcocapnos crassifolia, Curcuma longa, Linum usitatissimum, Vitis vinifera, Lithops pseudotruncatella, Arnica montana, Morinda citrifolia, Symphytum officinale, Cannabis sativa, Olea europaea*, and *Camellia sinensis*, said fraction:

comprising peptides from 4 to 300 amino acids length, selected from peptide plant growth factors, plant transcription factors, epigenetic factors and mixtures thereof, and without having cytoplasmic cell contents from the cell lysis and membranes and/or cell walls; and obtainable by a method comprising:
(a) growing the dedifferentiated plant cells from a friable callus in a liquid nutrient culture medium from 5 to 15 days, to obtain a conditioned media supporting the growth of the dedifferentiated plant cells;
(b) removing entire plant cells from the conditioned media without lysing the cells, to obtain a cell-free supernatant comprising peptides from 4 to 300 amino acids length; and
(c) carrying out a protein separation process by means of a separation technique selected from the group consisting of solid-phase extraction chromatography, size-exclusion chromatography, filtration, ultrafiltration, protein precipitation, and combinations thereof, to obtain a fraction of the cell-free supernatant.

As will be derived from the examples below, both the supernatant or any fraction thereof comprising plant growth factors of peptide nature and/or transcription factors and or epigenetic factors (from 4 to 300 amino acids length) are able to revert senescence processes in human old fibroblast cultures (from culture of more than 12-13, even 20 passes), thus promoting re-youth of cells according to different cell markers indicating the "age status" of the cell.

Use of these cell-free supernatants as defined above or of a fraction thereof, implies the advantage of being using a composition with low or null toxicity when applied over mammal skin (dermis and/or epidermis cells). This is due to the no presence of some immunogenic compounds from the inner of the cells or even from the membrane. In addition, these supernatant or fractions compositions are less complex than those derived from cell lysates and, therefore, the proportion of the active compounds (peptide plant growth factors, transcription factors or epigenetic factors) in relation to the whole components of the suspension is greater than in plant cell suspension lysates.

The peptides of interest are thus directly purified, in the sense that the compositions are naturally enriched with the peptides of interest. In addition, relating to plant extracts or solvent extracts from the cell suspension lysates, the use of the supernatants of the invention involve also the advantage that peptides can be easily recovered and in a higher proportion, without the presence of possible toxic compounds present in the extract, and always recovered due to the inherent complexity of the extracts and to the difficulties of separating non-active but skin damaging compounds (such as compounds producing allergic reactions over the skin).

Thus, another aspect of the invention is a skin topical composition which comprises an effective amount of a cell-free fraction of a supernatant of a dedifferentiated plant cell suspension culture as defined above, said fraction comprising peptides from 4 to 300 amino acids length selected from peptide plant growth factors, peptide plant transcription factors, epigenetic factors and mixture thereof, together with one or more appropriate topical pharmaceutically or cosmetically acceptable excipients or carriers.

The invention relates also to cell-free supernatant of a dedifferentiated plant cell suspension culture, or a fraction of said cell-free supernatant, for use in cosmetics, in particular for reverting senescence status of dermis and epidermis cells.

It is also noteworthy to realise that the cell-free supernatants of the invention, or even any fraction thereof for use according to the invention, can be obtained from culturing dedifferentiated plant cells, which are easily to be obtained and have been widely used for the production of particular secondary metabolites with active properties in cosmetics or in pharmacy. Moreover, this conditioned media without cells (cytoplasm contents and membranes and/or cell walls) contains a cocktail of compounds with evident effects even at low doses in relation with controls and reference compositions. Examples of compounds in the conditioned media (cell-free supernatant) include amino acids, lipids, carbohydrates, antioxidant compounds, some secreted secondary metabolites (mainly phenols, flavonoids, phenols, alkaloids, and phytosterols), the peptides from 4 to 300 amino acid length, among others that are listed below. Without being bound to any theory, the inventors propose the surprising re-youth effect (senescence reversion) due to a synergistic behaviour of the compounds found in the supernatants that supported cell culture, which compounds are the most similar to the real ones found in the extracellular matrix of a damaged plant tissue or of a plant cell in charge of proliferation or of regeneration. The invention supposes an evidence that so quite different organisms, plants and animals, really act similarly in front of regeneration/repair/ differentiation tissue processes, since those peptide or components from extracellular spaces from plants provoke similar effects on animal cells, as would do the equivalent peptides/components from animal origin (in particular those of the plasma).

DETAILED DESCRIPTION OF THE INVENTION

Figure 1:
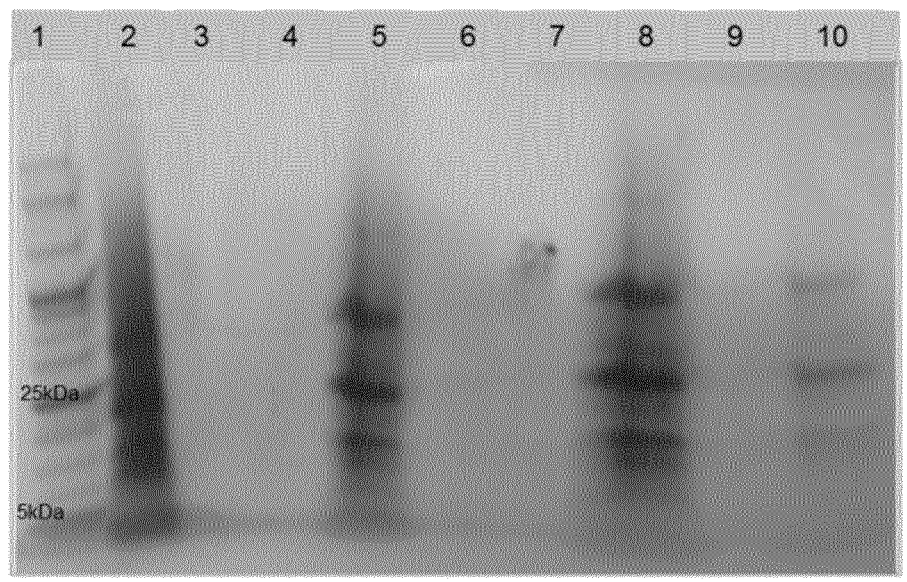
FIG. 1 is an image of SDS-PAGE electrophoresis of the cell-free supernatant of a culture of *Daucus carota* (Lyophilized samples 01, 02 and 03), and of two solid phase extractions (SPE 01, 02) fractions of the cell-free supernatant, comprising only compounds of peptide nature. Protein bands are detected by Comassie blue stainning.

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

The term "peptide plant growth factors" encompasses the so-called signalling polypeptides involved in plant defence, growth and development recently discovered and comprising sequences from 4 to 300 amino acids (See Ryan et al, supra; and Czyzewicz et al., infra). For peptide plant transcription factors are encompassed also peptides from 4 to 300 amino acids length, which in the plants from whom they derive act as regulators of shoot meristem formation, stem cell maintenance and somatic cell differentiation.

The expression "cell-free supernatant that previously supported the growth of a dedifferentiated plant cell suspension culture" refers only to the liquid that contained the dedifferentiated plant cells during growing or cultivation in suspension in a culture medium and for any purpose (production of secondary metabolites, biomass production, etc.). The cell-free supernatant does not contain the cytoplasm contents released from the lysis of the plant cells, as well as any part of the plant cell resulting from disruption of the same (membrane fragments, cell-wall fragments, etc.). The cell-free supernatant comprises among the ingredients of the initial culture medium that have been not consumed, also those compounds secreted by the plant cells to the extracellular media. Among these compounds there are the peptide plant growth factors. The cell-free supernatant is also called conditioned nutrient media or conditioned media, or conditioned cell-medium (used herewith interchangeably). When it is said that the cell-free supernatants are "without having cytoplasmic cell contents from the cell lysis and without having membranes and/or cell walls" is to be understood that traces of some membranes and/or cell walls, and cytoplasmic components (nucleic components, organelles, etc.) can be present due to the spontaneous disruption of isolated cells occurring occasionally during the culturing process.

By "fraction of cell-free supernatant comprising peptides from 4 to 300 amino acids length" is to be understood in the sense of the invention, a part (in particular a liquid part) of the initially recovered cell-free supernatant, which part has been purified by means allowing the recovery of peptides, such as chromatography technologies, sieve filtering or protein precipitations.

For "repairing and/or regenerating agents" is to be understood that the supernatants as well as any fractions thereof with the peptides from 4 to 300 amino acid length, have the ability to recover damaged still viable skin tissue (due to a wound, due to aging), as well as the ability to promote cell division from precursor skin cells to generate new tissue (also for example in a wound).

An "effective amount" of the cell-free supernatant or of a fraction thereof refers to the amount of active ingredients (at least the peptide plant growth factors of said supernatant or fraction) which provide a therapeutic or cosmetic effect after its application.

The term "pharmaceutically acceptable" refers to that excipients or carriers suitable for use in the pharmaceutical technology for preparing compositions with medical use.

The term "cosmetically acceptable" or "dermatological acceptable" which is herein used interchangeably refers to that excipients or carriers suitable for use in contact with human skin without undue toxicity, incompatibility, instability, allergic response, among others.

For "skin topical composition" is to be understood in the conventional sense to mean a composition that it is applied and performs effects to a predetermined area of skin or mucosa of a subject in need thereof, as in for example the treatment of several skin disorders. Topical administration is intended to provide local rather than a systemic effect. Topical composition means that it is applied on the skin, scalp and mucosae surfaces independently of the fact that the composition may reach the different skin layers (epidermis, dermis) or mucosa layers. The compositions of the invention are suitable for topical use on skin, scalp, and mucosa surfaces including oral mucosae, genital and anal mucosae.

The invention relates in a first aspect to cell-free supernatants that previously supported the growth of a dedifferentiated plant cell suspension culture, or a fraction of said cell-free supernatants, for use as a medicament for skin treatment, wherein said cell-free supernatant or said fraction comprises peptides from 4 to 300 amino acids length, and without having cytoplasmic cell contents from the cell lysis and without having membranes and/or cell walls.

In a particular embodiment, they are for use as cicatrisation skin agents, and/or for use as skin wound healing agent, and/or for use as skin re-youth agents. All these effects are due to the capability of the cell-free supernatants or fractions thereof of reverting senescence in dermis and epidermis cells. Thus, the cell-free supernatants or any fraction thereof with the peptides from 5 to 300 amino acids length are for use in the prophylaxis and/or treatment of a disease or condition which occurs through senescence of skin (dermis and/or epidermis cells), and selected from the group consisting of premature skin aging, skin cicatrisation, skin wound healing, and combination of these disorders. In another particular embodiment, they are for use in the treatment of a condition or disease selected from premature skin aging and photoaging, said conditions comprising fine and coarse wrinkles, irregular mottled pigmentation, brownish spots, roughness, yellowing and small superficial blood vessels called spider veins or telangiectasias, and combinations of all these conditions.

This could be also formulated as the skin topical use of the cell-free supernatant of a dedifferentiated plant cell suspension culture, or of a fraction thereof, both comprising peptides from 4 to 300 amino acids length selected from peptide plant growth factors and/or peptide plant transcription factors and/or epigenetic factors, particularly selected from peptide plant growth factors and/or peptide plant transcription factors, for the preparation of a medicament for the prophylaxis and/or treatment of a disease or condition which occurs through senescence of dermis and/or epidermis cells. It also relates to a method for the prophylaxis and/or treatment of a disease or condition which occurs through senescence of dermis and/or epidermis cells, which comprises administering to mammals in need of such treatment an effective amount cell-free supernatant of a dedifferentiated plant cell suspension culture, or of a fraction thereof, both comprising peptides from 4 to 300 amino acids length selected from peptide plant growth factors and/or peptide plant transcription factors and/or epigenetic factors, particularly selected from peptide plant growth factors and/or peptide plant transcription factors.

In other words, the cell-free supernatant that previously supported the growth of a dedifferentiated plant cell suspension culture, or a fraction of said cell-free supernatant are for use as topical skin treating agents, wherein the treating agent is as skin cicatrisation agent, and/or as skin wound healing agent, said cell-free supernatant or said fraction comprises peptides from 4 to 300 amino acids length, said peptides selected from peptide plant growth factors, plant transcription factors, epigenetic factors, and mixtures thereof, and said cell-free supernatant or said fraction without having cytoplasmic cell contents from the cell lysis and membranes and/or cell walls.

As will be depicted in the examples, cell senescence in fibroblasts of more than 20 passes was reverted to a younger phenotype when both, the plant cell-free supernatants of the invention and fractions of them comprising the peptide plant growth factors and/or peptide plant transcription factors and/or epigenetic factors, particularly plant growth factors and/or peptide plant transcription factors, were applied to the cultured senescent fibroblasts. Senescent or young phenotype of the initially senescent fibroblasts was determined by the expression levels of peroxiredoxin 4 and Poly-ADP ribose polymerase.

In another particular embodiment of the first aspect, the cell-free supernatants or a fraction of said cell-free supernatants for use as medicaments, comprise peptide plant growth factors from 4 to 300 amino acids, more in particular from 5 to 300 amino acids, even more in particular from 4 to 70 amino acids, particularly from 5 to 70 amino acids length. In another particular embodiment, they comprise peptide plant growth factors from 4 to 25 amino acids, even more in particular from 5 to 25 amino acids length. Length of the peptides (even of those that are plant transcription factors) is the parameter that conditions translocation through plant cell membrane and plant cell wall.

In yet another particular embodiment of this first aspect, the dedifferentiated plant cell culture suspension is from a plant selected from the group consisting of *Daucus carota, Centella asiatica, Punica granatum, Gossypium herbaceum, Sarcocapnos crassifolia, Curcuma longa, Linum usitatissimum, Vitis vinifera, Lithops pseudotruncatella, Arnica montana, Morinda citrifolia, Symphytum officinale, Cannabis sativa, Olea europaea*, and *Camellia sinensis*. More particularly, from a plant selected from the group consisting of *Daucus carota, Centella asiatica, Punica granatum, Gossypium herbaceum, Sarcocapnos crassifolia, Curcuma longa, Linum usitatissimum, Vitis vinifera, Lithops pseudotruncatella, Morinda citrifolia, Symphytum officinale, Cannabis sativa*, and *Olea europaea*. In another particular embodiment, the dedifferentiated plant cell culture suspension is from a plant selected from the group consisting of *Daucus carota, Centella asiatica*, and *Punica granatum*.

In another particular embodiment, optionally in combination with any embodiments above or below, the peptide plant growth factors are selected from the group consisting of Phytosulphokine-α (PSK-α), Phytosulphokine-β (PSK-β), Plant Peptide Containing Sulphated Tyrosine-1 (PSY1), Rapid Alkalinization Factor (RALF), Tracheary Element Differentiation Inhibitory Factor (TDIF), Clavata-3 (CLV3), Clavata-Embryo Surrounding Region-Related (CLE), Tapetum Determinant-1 (TPD1), Epidermal Patterning Factor-1 (EPF1), Inflorescence Deficient in Abscission (IDA), Embryo Surrounding Region-Related (ESR), Polaris peptide (PLS), Root meristem Growth Factor (RGF), Egg Cell-Secreted Protein (EC1), C-terminally Encoded peptide (CEP), Early Nodulin 40 (ENOD40), Systemin, S-locus Cystein Rich proteins (SCR), and mixtures thereof, which means a combination of all of them, of only two, three, four or more than two until comprising all of the listed peptides.

Other peptides than peptide plant growth factors are also present in a particular embodiment of the cell-free supernatants that previously supported the growth of a dedifferentiated plant cell suspension culture, or a fraction of said cell-free supernatants. These peptides are in particular peptide plant transcription factors, including among others Wound-Induced Dedifferentiation (WIND), Wuschel (WUS), Teosinte Branched1/Cycloidea/Proliferating Cell Factor (TCP), and transcriptional factor for root meristem maintenance (PLETHORA), and mixtures thereof. These transcription factors regulate shoot meristem formation, stem cell maintenance and somatic cell differentiation.

All of these peptide plant growth factors and peptide plant transcription factors appear disclosed for example in Czyzewicz et al., "Message in a bottle: small signalling peptide outputs during growth and development", Journal of Experimental Botany—2013, vol. no. 64(17), pp.: 5281-5296.

Traces of other compounds, usually known as epigenetic factors, are also comprised in the cell-free supernatants, or a fraction of said cell-free supernatants due to the residual disruption of some cells during culturing (as above enunciated), which can deliver the nuclear and cytoplasm contents in the culture media, although reduced to minimal amounts. Examples of these plant epigenetic factors are selected from the group consisting of Chromomethylase (CMT), Domains Rearranged Methyltransferase (DRM), Methyltransferase (MET), and some auxins, involved in the NA methylation processes; the chromatin remodelling factor PICKLE of the CHP family (the CHD proteins derive their name from the presence of three domains of sequence similarity: a Chromatin organization modifier domain (chromodomain), a SWI2/SNF2 ATPase/Helicase domain, and a motif with sequence similarity to a DNA-binding domain), the chromatin remodelling factor DDM1 (from Decrease In DNA Methylation-1), involved in decondensation and remodelling of chromatin; the histone H3 methyltransferase Kryptonite (KYP), involved in remodelling of histones; small RNA molecules; and mixtures of all these proteins and compounds. Epigenetic factors are to be understood as those biomolecules, particularly of peptide nature, that control marks in a cell for the DNA controlling expression or silencing of genes.

As above indicated the cell-free supernatant for use according to the invention further comprises compounds other than peptide plant growth factors, plant transcription factors and optionally plant epigenetic factors, secreted from the cells to the media. Indeed, this cell-free supernatant (that is, the conditioned media) comprise the compounds of the initial culture media that have not been consumed by the cells and those compounds that have been secreted by these plant cells during the growing in the culture media. Therefore, the cell-free supernatant according to the invention further comprises in a particular embodiment:

residual compounds of the media, such as proteins, lipids (such as fatty acids, phospholipids, and glycerides), polyalcohols (such as sorbitol and mannitol), auxins, glycoproteins and glycolipids, vitamins, compounds with antioxidant activity (NADH), inorganic salts, and carbohydrates (such as monosaccharides like glucose and fructose, disaccharides like sucrose, and oligo- and polysacharides); and optionally, secondary metabolites that cells may have been delivering to the media (such as flavonoids, phenols, alkaloids, phytosterols, and terpenoids (including plant carotenoids).

It is to be noted that in the cell-free supernatant that previously supported the growth of a dedifferentiated plant cell suspension culture (or in any fraction thereof), carbohydrates will be present in low amounts, since they have been consumed by the cells suspended in the media. Indeed, residual carbohydrate concentration is usually used for monitoring the growth of the culture, together with or independently with cell density as will be disclosed below. The skilled man knows how to monitor the growth of a cell suspension culture.

In another particular embodiment, optionally in combination with any embodiment above or below, the cell-free supernatant or fraction thereof for use as a medicament for skin treatment, is the one wherein said cell-free supernatant or fraction thereof is obtainable by a method comprising:

(a) growing dedifferentiated plant cells from a friable callus in a liquid nutrient culture medium from 5 to 15 days, to obtain a conditioned media supporting the growth of the dedifferentiated plant cells;

(b) removing entire plant cells from the conditioned media without lysing the cells, to obtain a cell-free supernatant comprising peptides from 4 to 300 amino acids length; and (c) optionally carrying out a protein separation process by means of a separation technique selected from the group consisting of chromatography, filtration, ultrafiltration, protein precipitation, and combinations thereof, to obtain a fraction of the cell-free supernatant.

In more particular embodiment, the cell-free supernatant is obtainable by a method comprising in step (a) growing dedifferentiated plant cells from a friable callus in a liquid nutrient culture medium from 10 to 12 days, to obtain a conditioned media supporting the growth of the dedifferentiated plant cell.

As indicated, an alternative way of performing step (a) to obtain the conditioned media (cell-free supernatant) is by controlling the concentration of carbohydrates (for example sucrose) in the culture media, which concentration is decreased along time due to cell consumption. Another alternative way of controlling the growth of dedifferentiated plant cells in the suspension culture is by determining cell density in the culture (number of cells/ml of culture). Thus, in another particular embodiment of the first aspect, optionally in combination with any embodiments above or below, the cell-free supernatant is the one supporting a dedifferentiated plant cell suspension culture, wherein cell density (expressed as number of cells per volume unit of suspension culture) is from, from $1.10^5$ cell/ml of suspension culture to $1.10^7$ cell/ml suspension culture, more particularly from $1.10^6$ cell/ml of suspension culture to $3.10^6$ cell/ml suspension culture.

In another particular embodiment, the cell-free supernatant for use as a medicament and as above indicated is obtainable by a method comprising prior to step (a), a step of dedifferentiating a plant cell from a plant tissue by in vitro submitting it to a dedifferentiating media comprising plant growth regulators selected from auxins, cytokinins, gibberellins, and mixtures thereof.

Among particular methods for removing entire plant cells from the conditioned media without lysing them, there are encompassed sedimentation of cells by gravity, centrifugation (particularly from 4000 to 4600 rpm), filtration through mesh or filters for retaining cells and collect the supernatant, and precipitation of solids (cells).

In another particular embodiment of the first aspect, optionally in combination with any embodiments above or below, the cell-free supernatant or fraction is the one that is obtainable by a method as disclosed above and comprising after step (b) a freeze-drying step of the cell-free supernatant, to obtain a freeze-dried supernatant. In a more particular embodiment, this freeze-dried cell-free supernatant is concentrated from 10 to 30 times. Concentration of the freeze-dried supernatant can be achieved, for example, by re-suspending the entire freeze-dried supernatant in a volume of a solvent solution (generally a buffered solution) which volume is lower than the initial cell-free supernatant volume before being freeze-dried.

Other particular embodiments of the first aspect of the invention, optionally in combination with any embodiments above or below, encompass cell-free supernatants for use as medicaments for topical skin treatment, wherein the dedifferentiated plant cell suspension culture is submitted to stress conditions by means of elicitation processes to enhance production of secondary metabolites. Particular elicitation processes include elicitation with biotic elicitors selected from yeast cell wall, mycelia wall, fungal spores, polysaccharides (such as alginate, pectin, and chitosan), oligosaccharides, cyclodextrins, peptides and proteins (such as glutathione, cellulases, elicitins, pectinase, and protein kinases), low-molecular-weight organic acids (such as acetic acid, valeric acid, oxalic acid, lactic acid, citric acid, and malic acid), volatiles, jasmonate compounds (such as methyl jasmonate), and salicilates. Other particular elicitation processes include elicitation with abiotic elicitors selected from UV-radiation, IR-radiation, ozonation, microwaves, ultrasounds, temperature, osmotic stress (high salinity), redox environment, visual light wavelengths, inorganic salts, disturbed circadian rhythm processes, and photo-periods.

Due to the effect on the dermis (fibroblast), and epidermis (keratinocytes) cells, when cell-free supernatants or a fraction thereof with the peptides from 4 to 300 amino acids are applied onto the skin (topically), the whole skin aspect ameliorates. Therefore, a cosmetic use is also inferred, more in particular a re-youth effect on skin. It is thus also part of the invention the use of a cell-free supernatant that previously supported the growth of a dedifferentiated plant cell suspension culture, or a fraction of said cell-free supernatant as topical skin re-youth agent, wherein said cell-free supernatant or said fraction comprises peptides from 4 to 300 amino acids length, said peptides selected from peptide plant growth factors, plant transcription factors, epigenetic factors and mixtures thereof, and said cell-free supernatant or said fraction without having cytoplasmic cell contents from the cell lysis and membranes and/or cell walls.

In particular, the cosmetic use implies using the dedifferentiated plant cell culture suspension from a plant selected from the group consisting of *Daucus carota, Centella asiatica, Punica granatum, Gossypium herbaceum, Sarcocapnos crassifolia, Curcuma longa, Linum usitatissimum, Vitis vinifera, Lithops pseudotruncatella, Arnica montana, Morinda citrifolia, Symphytum officinale, Cannabis sativa, Olea europaea,* and *Camellia sinensis.* More particularly, from a plant selected from the group consisting of *Daucus carota, Centella asiatica, Punica granatum, Gossypium herbaceum, Sarcocapnos crassifolia, Curcuma longa, Linum usitatissimum, Vitis vinifera, Lithops pseudotruncatella, Morinda citrifolia, Symphytum officinale, Cannabis sativa,* and *Olea europaea.*

More particularly, in the use according to the invention, the cell-free supernatant or fraction thereof is obtainable by a method comprising:
  (a) growing dedifferentiated plant cells from a friable callus in a liquid nutrient culture medium from 5 to 15 days, to obtain a conditioned media supporting the growth of the dedifferentiated plant cells;
  (b) removing entire plant cells from the conditioned media without lysing the cells, to obtain a cell-free supernatant comprising peptides from 4 to 300 amino acids length, said peptides selected from peptide plant growth factors, plant transcription factors, epigenetic factors and mixtures; and
  (c) optionally carrying out a protein separation process by means of a separation technique selected from the group consisting of chromatography, filtration, ultrafiltration, protein precipitation, and combinations thereof, to obtain a fraction of the cell-free supernatant.

The cell-free supernatant or fraction thereof when used as cosmetic re-youth agent are in particular obtainable by a method comprising freeze-drying the cell-free supernatant after step (b) to obtain a freeze-dried supernatant. In addition, these cell-free supernatants or fractions thereof are obtainable by further concentrating from 100 to 500 times the obtained freeze-dried cell-free supernatant. As above indicated for the medical use, the dedifferentiated plant cell suspension culture is cultured at a cell density, expressed as number of cells per volume unit of suspension culture, from $1.10^5$ cell/ml of suspension culture to $1.10^7$ cell/ml suspension culture. Further and optionally, the dedifferentiated plant cell suspension culture is submitted to stress conditions by means of elicitation processes.

When the fractions of the cell-free supernatants are used as topical skin re-youth agents, said fractions are from a cell free-supernatant that previously supported the growth of a dedifferentiated plant cell suspension culture is from a plant selected from the group consisting of *Daucus carota, Centella asiatica, Punica granatum, Gossypium herbaceum, Sarcocapnos crassifolia, Curcuma longa, Linum usitatissimum, Vitis vinifera, Lithops pseudotruncatella, Arnica montana, Morinda citrifolia, Symphytum officinale, Cannabis sativa, Olea europaea*, and *Camellia sinensis*, said fraction:

comprising peptides from 4 to 300 amino acids length, said peptides selected from peptide plant growth factors, plant transcription factors, epigenetic factors, and mixtures thereof, and the fraction without having cytoplasmic cell contents from the cell lysis and membranes and/or cell walls; and obtainable by a method comprising:
(a) growing the dedifferentiated plant cells from a friable callus in a liquid nutrient culture medium from 5 to 15 days, to obtain a conditioned media supporting the growth of the dedifferentiated plant cells;
(b) removing entire plant cells from the conditioned media without lysing the cells, to obtain a cell-free supernatant comprising peptides from 4 to 300 amino acids length; and
(c) carrying out a protein separation process by means of a separation technique selected from the group consisting of solid-phase extraction chromatography, size-exclusion chromatography, filtration, ultrafiltration, protein precipitation, and combinations thereof, to obtain a fraction of the cell-free supernatant.

As above exposed, the invention also has as an object a fraction of a cell free-supernatant that previously supported the growth of a dedifferentiated plant cell suspension culture from a plant selected from the group consisting of *Daucus carota, Centella asiatica, Punica granatum, Gossypium herbaceum, Sarcocapnos crassifolia, Curcuma longa, Linum usitatissimum, Vitis vinifera, Lithops pseudotruncatella, Arnica montana, Morinda citrifolia, Symphytum officinale, Cannabis sativa, Olea europaea*, and *Camellia sinensis*. More particularly, from a plant selected from the group consisting of *Daucus carota, Centella asiatica, Punica granatum, Gossypium herbaceum, Sarcocapnos crassifolia, Curcuma longa, Linum usitatissimum, Vitis vinifera, Lithops pseudotruncatella, Morinda citrifolia, Symphytum officinale, Cannabis sativa*, and *Olea europaea*. Said fraction comprises peptides from 4 to 300 amino acids length and without comprising cytoplasmic cell contents from the cell lysis and membranes and/or cell walls.

In a particular embodiment of this cell-free faction obtainable by a method as defined above, step (c) is carried out by means of solid-phase extraction (abbreviated SPE) chromatography. More in particular an SPE allowing recovering of peptides from the cell-free supernatant with a molecular weight lower than 30 kDa. Among these peptides there are peptide plant growth factors, epigenetic factors and plant transcription factors.

Other particular cell-free fractions of the supernatants also obtainable by SPE, or by SPE in combination with another protein separation process as above disclosed include those fractions with peptides with a molecular weight lower than 10 kDa or even lower than 3 kDa. Considering a median molecular weight per amino acid of 110 Da, these fractions of the invention obtainable by SPE comprise peptides from 30 to 300 amino acids length.

Depending on the combinations of the protein separation techniques, fractions with peptides of different size (amino acid length) can be isolated from the cell-free supernatant. Thus, particular fractions have peptides from 4 to 1000 amino acids length, 5 to 1000 amino acids length, other from 5 to 50 amino acids length, or from 4 to 300 amino acids length, or from 5 to 300 amino acids length, or from 4 to 100 amino acids length, or from 5 to 100 amino acids length, or from 4 to 30 amino acids length, or from 5 to 30 amino acids length.

In another particular embodiment of the fractions of the invention, optionally in combination with any embodiment above or below, the filtration technique is the tangential flow filtration (TFF). This technique uses filters with different size pores (molecular weight cuts) for fractioning a test sample according to the pore sizes. TFF gets its name because the majority of the feed flow travels tangentially across the surface of the filter, rather than into the filter. The principal advantage of this is that the filter cake (which can blind the filter) is substantially washed away during the filtration process, increasing the length of time that a filter unit can be operational. It can be a continuous process, unlike batch-wise dead-end filtration. Filters may be of cellulose acetate or of polyethersulphone.

In a particular embodiment, the fractions comprise peptide plant growth factors selected from the group consisting of Phytosulphokine-α (PSK-α), Phytosulphokine-β (PSK-β), Plant Peptide Containing Sulphated Tyrosine-1 (PSY1), Rapid Alkalinization Factor (RALF), Tracheary Element Differentiation Inhibitory Factor (TDIF), Clavata-3 (CLV3), Clavata-Embryo Surrounding Region-Related (CLE), Tapetum Determinant-1 (TPD1), Epidermal Patterning Factor-1 (EPF1), Inflorescence Deficient in Abscission (IDA), Embryo Surrounding Region-Related (ESR), Polaris peptide (PLS), Root meristem Growth Factor (RGF), Egg Cell-Secreted Protein (EC1), C-terminally Encoded peptide (CEP), Early Nodulin 40 (ENOD40), Systemin, S-locus Cystein Rich proteins (SCR), and mixtures thereof, which means a combination of all of them, of only two, three, four or more than two until comprising all of the listed peptides. In another particular embodiment of the fractions of the invention, optionally in combination with any embodiment above or below, the peptide plant transcription factors are selected from the Wound-Induced Dedifferentiation transcription factor (WIND), Wuschel (WUS) transcription factor, Teosinte Branched1/Cycloidea/Proliferating Cell Factor (TCP), and transcriptional factor for root meristem maintenance (PLETHORA), and mixtures thereof. In another particular embodiment of the fractions of the invention, optionally in combination with any embodiment above or below, the epigenetic factors are selected from the group consisting of Chromomethylase (CMT), Domains Rearranged Methyltransferase (DRM), Methyltransferase (MET), and some auxins, involved in the NA methylation processes; the chromatin remodelling factor PICKLE of the CHP family (the CHD proteins derive their name from the presence of three domains of sequence similarity: a Chromatin organization modifier domain (chromodomain), a SWI2/SNF2 ATPase/Helicase domain, and a motif with sequence similarity to a DNA-binding domain), the chromatin remodelling factor DDM1 (from Decrease In DNA Methylation-1), involved in decondensation and remodelling of chromatin; the histone H3 methyltransferase Kryptonite (KYP), involved in remodelling of histones; small RNA molecules; and mixtures of all these proteins and compounds.

Both, the cell-free supernatants of a dedifferentiated plant cell suspension culture for use according to the invention, and any fraction thereof are, in a particular embodiment, provided as lyophilized compositions. In another particular embodiment they are in liquid form.

The invention encompasses skin topical composition which comprise an effective amount of any of these cell-free fraction of a supernatant of a dedifferentiated plant cell suspension culture as defined above, said fraction comprising peptides from 4 to 300 amino acids length selected from peptide plant growth factors, peptide plant transcription factors, plant epigenetic factors and mixture thereof, together with one or more appropriate topical pharmaceutically or cosmetically acceptable excipients or carriers.

The skin topical compositions of the invention can be used for the care of the skin. Thus, the present invention encompasses also the topical use of a cell-free supernatant of a dedifferentiated plant cell suspension culture, or of a fraction of said cell-free supernatant comprising peptide plant growth factors and/or peptide plant transcription factors and/or epigenetic factors as defined above, as a skin care agent, wherein the skin care comprises ameliorating at least one of the following symptoms, by means of reverting senescence of dermis and/or epidermis cells: roughness, flakiness, dehydration, tightness, chapping, elasticity, and itch of the skin. Skin care is in particular for premature skin aging and photoaging.

In another particular embodiment, optionally in combination with any embodiments above or below, the topical compositions comprises glycerine as pharmaceutically or cosmetically acceptable excipients or carriers. In another particular embodiment, the topical pharmaceutically or cosmetically excipient or carrier is selected from the group consisting of a skin barrier recovery agent, an hydrating agent, an emollient, an emulsifier, a thickener, an humectant, a pH-regulating agent, an antioxidant, a preservative agent, a vehicle, and a mixture thereof.

The invention also encompasses cell-free supernatants of a dedifferentiated plant cell suspension culture of *Daucus carota* or of a *Daucus* genera plant, or a fraction of said cell-free supernatant, said supernatant and fraction comprising peptide plant growth factors and/or peptide plant transcription factors and/or epigenetic factors from 4 to 300 amino acids length, particularly from 5 to 300 amino acids length, and without having cytoplasmic cell contents from the cell lysis and membranes and/or cell walls. These supernatants and fractions of *Daucus carota* or of a *Daucus* genera plant, are for use in cosmetics and as medicaments. In a particular embodiment, they are for use in cosmetics or as medicaments for reverting senescence status of dermis, and epidermis cells of skin, thus they are for use in the treatment of a condition or disease selected from premature skin aging and photoaging, said conditions comprising fine and coarse wrinkles, irregular mottled pigmentation, brownish spots, roughness, yellowing and small superficial blood vessels called spider veins or telangiectasias, and combinations of all these conditions. In particular, they are for use in reverting senescence in fibroblasts. These supernatants and fractions of *Daucus carota* or of a *Daucus* genera plant, are in a particular embodiment obtainable as disclosed above for any plant cell culture. These supernatants and fractions of *Daucus carota* or of a *Daucus* genera plant, can be comprised in skin topical compositions in effective amounts, together with one or more appropriate topical pharmaceutically or cosmetically acceptable excipients or carriers.

The invention also encompasses cell-free supernatants of a dedifferentiated plant cell suspension culture of *Centella asiatica*, or of a *Centella* genera plant or a fraction of said cell-free supernatant, said supernatant and fraction comprising peptide plant growth factors and/or peptide plant transcription factors and/or epigenetic factors from 4 to 300 amino acids length, particularly from 5 to 300 amino acids length, and without having cytoplasmic cell contents from the cell lysis and membranes and/or cell walls. These supernatants and fractions of *Centella asiatica*, or of a *Centella* genera plant, are for use in cosmetics and as medicaments. In a particular embodiment, for use in cosmetics or as medicaments for reverting senescence status of dermis and epidermis cells of skin, thus they are for use in the treatment of a condition or disease selected from premature skin aging and photoaging, said conditions comprising fine and coarse wrinkles, irregular mottled pigmentation, brownish spots, roughness, yellowing and small superficial blood vessels called spider veins or telangiectasias, and combinations of all these conditions. In particular, for reverting senescence in fibroblasts. These supernatants and fractions of *Centella asiatica*, or of a *Centella* genera plant, are in a particular embodiment obtainable as disclosed above for any plant cell culture. These supernatants and fractions of *Centella asiatica*, or of a *Centella* genera plant, can be comprised in topical pharmaceutical or cosmetically compositions in effective amounts, together with one or more appropriate topical pharmaceutically or cosmetically acceptable excipients or carriers.

The invention also encompasses cell-free supernatants of a dedifferentiated plant cell suspension culture of *Punica granatum*, or of a *Punica* genera plant, or a fraction of said cell-free supernatant, said supernatant and fraction comprising peptide plant growth factors and/or peptide plant transcription factors and/or epigenetic factors from 4 to 300 amino acids length, particularly from 5 to 300 amino acids length, and without having cytoplasmic cell contents from the cell lysis and membranes and/or cell walls. These supernatants and fractions of *Punica granatum* or of a *Punica* genera plant, are for use in cosmetics and as medicaments. In a particular embodiment, for use in cosmetics or as medicaments for reverting senescence status of dermis and epidermis cells of skin, thus they are for use in the treatment of a condition or disease selected from premature skin aging and photoaging, said conditions comprising fine and coarse wrinkles, irregular mottled pigmentation, brownish spots, roughness, yellowing and small superficial blood vessels called spider veins or telangiectasias, and combinations of all these conditions. In particular, for reverting senescence in fibroblasts. These supernatants and fractions of *Punica granatum*, or of a *Punica* genera plant, are in a particular embodiment obtainable as disclosed above for any plant cell culture. These supernatants and fractions of *Punica granatum*, or of a *Punica* genera plant, can be comprised in topical pharmaceutical or cosmetically compositions in effective amounts, together with one or more appropriate topical pharmaceutically or cosmetically acceptable excipients or carriers.

The invention also encompasses cell-free supernatants of a dedifferentiated plant cell suspension culture of *Gossypium herbaceum*, or of a *Gossypium* genera plant, or a fraction of said cell-free supernatant, said supernatant and fraction comprising peptide plant growth factors and/or peptide plant transcription factors and/or epigenetic factors from 4 to 300 amino acids length, particularly from 5 to 300 amino acids length, and without having cytoplasmic cell contents from the cell lysis and membranes and/or cell walls. These supernatants and fractions of *Gossypium herbaceum*, or of a *Gossypium* genera plant, are for use in cosmetics and as medicaments. In a particular embodiment, for use in cosmetics or as medicaments for reverting senescence status of dermis and epidermis cells of skin, thus they are for use in the treatment of a condition or disease selected from premature skin aging and photoaging, said conditions comprising fine and coarse wrinkles, irregular mottled pigmentation, brownish spots, roughness, yellowing and small superficial blood vessels called spider veins or telangiectasias, and combinations of all these conditions. In particular, for reverting senescence in fibroblasts. These supernatants and fractions of *Gossypium herbaceum* or of a *Gossypium* genera plant, are in a particular embodiment obtainable as disclosed above for any plant cell culture. These supernatants and fractions of *Gossypium herbaceum*, or of a *Gossypium* genera plant, can be comprised in topical pharmaceutical or cosmetically compositions in effective amounts, together with one or more appropriate topical pharmaceutically or cosmetically acceptable excipients or carriers.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Example 1

Assay of Cell-Free Supernatants and Fractions Thereof with Peptides from 4 to 300 Amino Acids Length on a Model of Old Skin (Human Dermal Fibroblasts of More than 20 Passes in Dulbecco's Culture)

1.1 Method for Obtaining Cell-Free Supernatants.

Cell suspension cultures from *Daucus carota*, *Punica granatum* and *Centella asiatica*, were obtained from inoculums of cell suspensions grown at 200 ml The inoculums (⅕ of inoculum in relation to the total volume of culture) were inoculates into 2000-ml flasks containing 800 ml of MS liquid medium supplemented with 20-30 g/L of sucrose (for example, 30 g), and hormones (for *Daucus carota* 1-3 mg/L of 2,4-D; for *Punica granatum* 0.2 mf/L of naphthalene acetic acid (ANA) and 1 mg/L of kinetin; and for *Centella asiatica* 2 mg/L of 2,4-D and between 0.1 mg/L of BAP) and placed in a rotary shaker at 100 rpm in the dark at 25° C. Cell cultures were grown for 12 days, when they were clarified (i.e. the cells were removed avoiding lysis) by centrifugation at 4600 rpm for 10 min, to obtain the conditioned media, which was further studied.

400 mL of the three samples were dispensed in beakers for lyophilisation (freeze-drying), frozen –80° C. and lyophilized overnight.

Lyophilized products were concentrated from 400 mL to 20 mL in saline buffer, and from this volume, 1 mL was taken for analysis (see below). Therefore initially lyophilized products were 20 times concentrated once tested over HDF.

1.2. Fractions of Conditioned Media (CM) Comprising Peptide Plant Growth Factors and/or Peptide Plant Transcription Factors and/or Epigenetic Factors (Cell Factors)

Prior to fractioning, each of the CM (cell-free supernatants) of 1.1 were analysed for determining peptide size spectra (what it is also known as protein fingerprinting). Thus electrophoresis in denaturing protein conditions (SDS-PAGE) was performed with each CM. This allowed visualizing approximate molecular weights of the protein and peptides present in the cell-free supernatants of each plant species.

In order to recover the fractions of cell-free supernatants comprising the peptides with the desired molecular weight ranges, chromatographic techniques were performed.

To this aim, 400 mL of the samples were used for solid-phase extraction (SPE) in OASIS HLB cartridges (previously conditioned with 1 column volume (CV) of trifluoroacetic acid (TFA) 0.1% in HPLC water, 1CV TFA 0.1% in HPLC acenonitrile (ACN) and 1CV of TFA 0.1% in HPLC water). Residual volume from input, FT, Wash was kept.

SPE allowed recovering from CM only the proteins and peptides, and it already excluded >30 kDa proteins (similar to 30 kDa membranes efficiency), thus there were recovered fractions of the conditioned media of *Daucus carota*, *Centella asiatica* and *Punica granatum* comprising peptides (plant growth factors and plant transcription factors and epigenetic factors) with a molecular weight range from 0 to 30 kDa (fractions with peptides from 5 to 300 amino acids length).

Elution of SPE was performed in 1CV TFA 0.1% in HPLC ACN and dried at 65° C. for 2 h.

All fractions and dried intermediate products were kept at +4° C. overnight.

Dried products from SPE were re-suspended in 2 mL of saline buffer. Thus, fractions were concentrated 200-times. Samples were then analysed by total protein and SDS-PAGE, according to next table 1 data (FIG. 1 shows also the Comassie blue peptide bands in each electrophoresis lane for the conditioned media and SPE fractions of *Daucus carota*, *Centella asiatica* and *Punica granatum*).

Table 1: Detailed identification of lanes in the SDS-PAGE electrophoresis of *Daucus carota*, *Centella asiatica* and *Punica granatum* lyophilised conditioned media (CMs) (Lyophilised 01, 02, 03, respectively) and of SPE fractions from cell-free supernatants (elute 01 of *Daucus carota* and elute 02 of *Centella asiatica*)

| Lane | Sample code | Sample description | Load |
|---|---|---|---|
| 1 | N/A | MW Ladder | 2.5 ug |
| 2 | 170215-01 | Lyophilised 01 | 5 ug |
| 3 | 170215-02 | Lyophilised 02 | <1 ug |
| 4 | N/A | N/A | N/A |
| 5 | 170215-03 | Lyophilised 03 | 5 ug |
| 6 | N/A | N/A | N/A |
| 7 | N/A | N/A | N/A |
| 8 | 160215-01 | SPE elute 01 | 5 ug |
| 9 |  | N/A |  |
| 10 | 160215-02 | SPE elute 02 | <5 ug |

The materials for performing protein separation in any of experimental data 1.1 and 1.2 were:
Material
TFA 0.1% in HPLC water
TFA 0.1% in HPLC ACN
OASIS HLB cartridges
Biorad protein Quantitation kit
Tris Glycine 4-12% PAGE gel
Tris Glycine Sample buffer 2× plus DTT
Tris glycine Running bufer 1×
Saline buffer (Ringer or phosphate buffer)

Equipment
   Centrifuge
   Vaccum System
   Freezer −80° C.
   Lyophylisation equipment
   Electrophoresis System
   Plate reader Protein analysis was performed using Biorad protein Quantitation kit (the protocol used was the recommended by Bio Rad under http://www.biorad.com/webroot/web/pdf/lsr/literature/Bulletin_9004.pdf) and SDS PAGE analysis to determine the total protein concentration in each sample.

1.3. Test of Cell-Free Supernatants and of Fractions Thereof Over a Model of Old Skin (Human Derman Fibroblasts of More Than 20 Passes in Dulbeccos's; Replicative Senescence)

In order to test the effect of the cell-free supernatants as well as of the fractions thereof a culture of old human dermal fibroblasts (HDF) was used.

rigidity and irregularity, increased number of vacuoles), decreased proliferative index (Doubling time>60 h) and β-Gal positive staining. Juvenile HDF were used at passage #3 to 5 in all performed experiments.

Efficacy Studies:

Cell culture conditions: Juvenile and Senescent HDF were seeded in cell culture 12-well plates (Corning), at a density of 25,000 cells/well (6.2·103 cells/cm2) in Growth Medium, and were then cultivated during 24-48 hours at the cell culture standard conditions: 37° C., 5% CO2 & 90% RH.

Test compound preparation: Test products were prepared at the defined final concentrations by its dilution in Maintenance Medium (Dulbecco's 1 g/L glucose medium, supplemented with 1% foetal bovine serum (FBS, PAA); 2 mM L-glutamine (Lonza); and antibiotics (100 µg/ml Penicillin and 100 U/ml of Streptomycin, Lonza), just before each application.

Evaluated Concentrations:

| Test products | Evaluated conc. | C1 | C2 | C3 | C4 | C5 | C6 |
|---|---|---|---|---|---|---|---|
| *D. Carota* (traditional extract) | mg/ml | 1.25 | 0.625 | 0.31 | — | — | — |
| *D. Carota* (PHYTURE) | mg/ml | 1.25 | 0.63 | 0.31 | — | — | — |
| *P. Granatum* (traditional extract) | mg/ml | 0.00938 | 0.005 | 0.0023 | 1.9E−05 | 9.4E−06 | 4.7E−06 |
| *P. Granatum* (PHYTURE) | mg/ml | 0.01875 | 0.00938 | 0.00469 | — | — | — |
| SPE elute 01 (*Daucus carota*) | µg/ml | 1 | 0.5 | 0.25 | — | — | — |
| SPE elute 02 (*Centella asiatica*) | µg/ml | Dil. 1/3 | Dil. 1/6 | Dil. 1/12 | — | — | — |
| SPE elute 03 (*Punica granatum*) | µg/ml | 0.5 | 0.25 | 0.125 | — | — | — |
| Lyo 01 (*Daucus carota*) | µg/ml | 0.5 | 0.25 | 0.125 | — | — | — |
| Lyo 02 (*Centella asiatica*) | µg/ml | 10 | 1 | 0.5 | — | — | — |
| Lyo 03 (*Punica granatum*) | µg/ml | 0.1 | 0.05 | 0.025 | — | — | — |
| Ellagic acid | µg/ml | 3.75 | 1.875 | 0.9375 | 0.0075 | 0.00375 | 0.00188 |

Cell Model:

Normal Human Dermal Fibroblasts (HDF) were obtained from foreskin samples, surpluses from surgery of young donors (0-3 years old) and stablished by using the standard method of explants growth and enzymic dissociation of proliferating cells. Cells were propagated and grown in Growth Medium (GM): Dulbecco's 1 g/L glucose medium, supplemented with 10% foetal bovine serum (FBS, PAA); 2 mM L-glutamine (Lonza); and antibiotics (100 µg/ml Penicillin and 100 U/ml of Streptomycin, Lonza). For routine subcultivation and propagation of the primary culture, cells were washed twice with PBS (Phosphate Phosphate buffered saline, pH 7.4), harvested with trypsin-EDTA (Gibco) and counted in Neubauer chamber before its seeding in a new cell culture flask (Falcon, 75 cm2).

In order to obtain senescent HDF, the primary culture was then subcultivated repeatedly at each time it becomes a confluence of 80-90%, by means of routine subcultivation method. In all the performed experiments, the senescent HDF were used at passage/subcultivation #22 to 26. These cells were previously characterized and showed clearly senescent phenotype: morphological and structural changes (increased cell size, change of shape from thin, long, and spindle-like to flattened and irregular, increased membrane Cell Treatment:

Cells were treated with test products for 8 days, with applications every 2-3 days (N° Total applications: 3).

Test Controls:
1) Non-treated senescent HDF in Maintenance Medium: Cells cultured in Maintenance Medium during treatment period. The medium was removed every 2-3 days. This condition is the reference that indicates cell basal levels of the different markers/proteins evaluated.
2) Non-treated senescent HDF in Growth Medium: Cells cultured in Growth Medium during treatment period. The medium was removed every 2-3 days. This condition is an internal positive control, as it shows the effect of growth factors, cofactors and proteins in the foetal bovine serum used as medium supplement.
3) Non-treated juvenile HDF in Maintenance Medium: HDF juvenile cultured in Maintenance Medium during treatment period. The medium was removed every 2-3 days. This experimental condition indicates levels of the different markers/proteins evaluated in young cells in maintenance medium (medium with low concentration of foetal bovine serum).
4) Non-treated juvenile HDF in Growth Medium: HDF juvenile cultured in Growth Medium during treatment period. The medium was removed every 2-3 days. This experimental condition indicates the maximum level of the different markers/proteins evaluated in young cells in optimal culture conditions.

Figure 2:
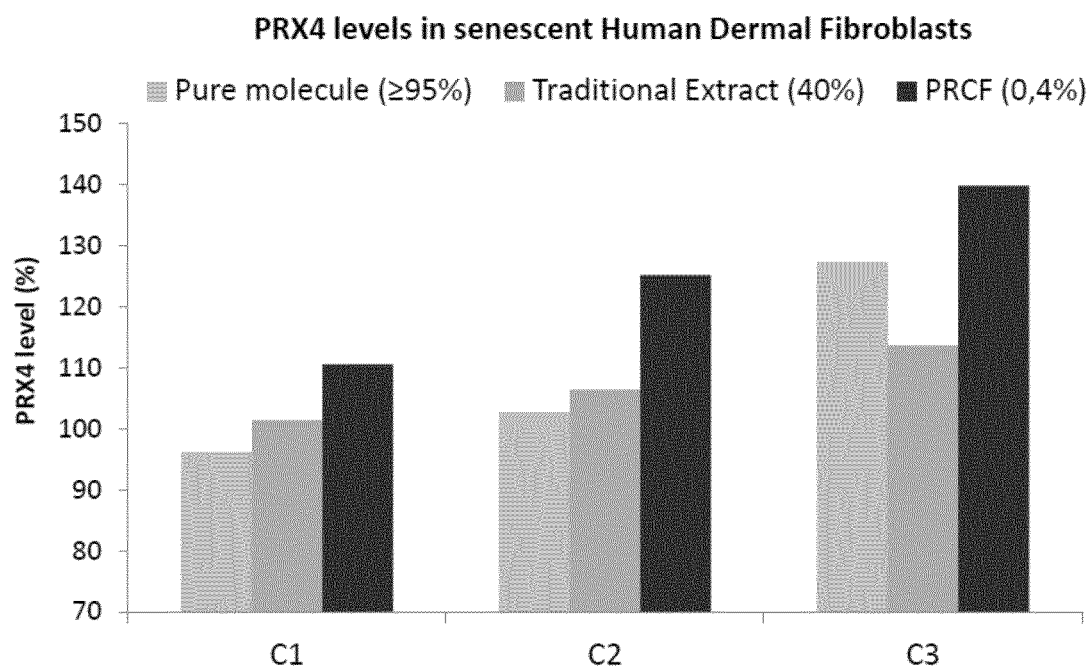
FIG. 2 is a graph showing the levels in percentage (%) of peroxiredoxin 4 (PRX4) in HDF. Peroxiredoxin 4 is a marker increased in human dermal fibroblasts (HDF) reverting a senescent phenotype to a younger one phenotype. Peroxiredoxin 4 was measured by an ELISA assay. There were tested a composition of ellagic acid (>95%, named pure molecule), left bar in each concentration; an extract of (40% ellagic acid) of *Punica granatum* (containing 40% ellagic acid, named PRCF), middle-bar in each concentration; and a *Punica granatum* cell lysate (containing 0.4% ellagic acid), right-bar in each concentration. The tested concentrations of each sample over the HDF were: C1 (0.0019 µg/ml) C2 (0.00375 µg/ml) and C3 (0.0075 µg/ml). The PRCF (from plasma rich in cell factors) proceeds from a dried cell lysate of *Punica granatum* and it contains, among other substances present in the media and not consumed by the cells in suspension, the peptide plant growth factors and the peptide plant transcription factors (both termed herewith by way of simplification as cell factors), but also the contents of cell cytoplasm, membranes and cell wall fragments.

Firstly, for illustrating the source of the effective compositions of the invention, the inventors performed an assay to show that cell-suspension cultures and derivatives (cell lysates) are powerful source of active compounds. To do this, there were tested over HDF (senescent fibroblasts by replicative senescence, more than 20 passes) several concentrations of several active compositions. The tested compositions and data are depicted in FIG. 2. Briefly, the compositions were: ellagic acid (>95%, named pure molecule), left bar in each concentration; an extract of (40% ellagic acid) of *Punica granatum* (containing 40% ellagic acid, named PRCF), middle-bar in each concentration; and a *Punica granatum* cell lysate (containing 0.4% ellagic acid), right-bar in each concentration.

The data show the levels in percentage (%) of peroxiredoxin 4. Peroxiredoxin 4 is a marker increased in human dermal fibroblasts (HDF) reverting a senescent phenotype to a younger one phenotype. Peroxiredoxin 4 was measured by an ELISA assay.

Figure 5:
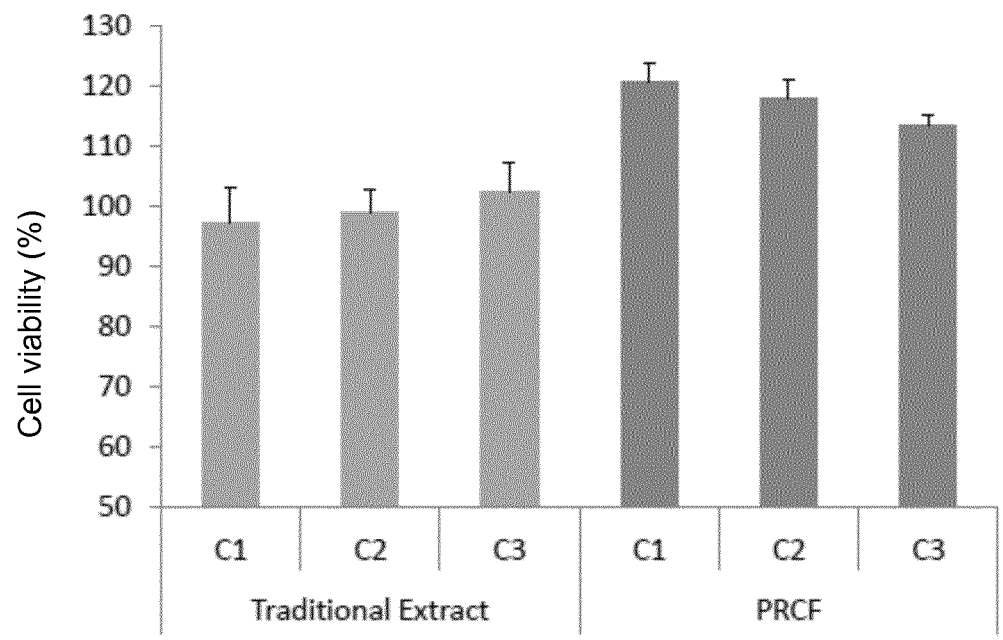
FIG. 5 is a graph showing the cell viability (% of living cells measured as final count/initial count by means of cell staining) in HDF (more than 20 passes). There are compared in panel the extracts of *Daucus carota* (panel A) and *Punica granatum* (panel B) with the cell lysates of each specie (PRCF) at the same concentrations (C1 to C3) of FIG. 1.
Figure 5:
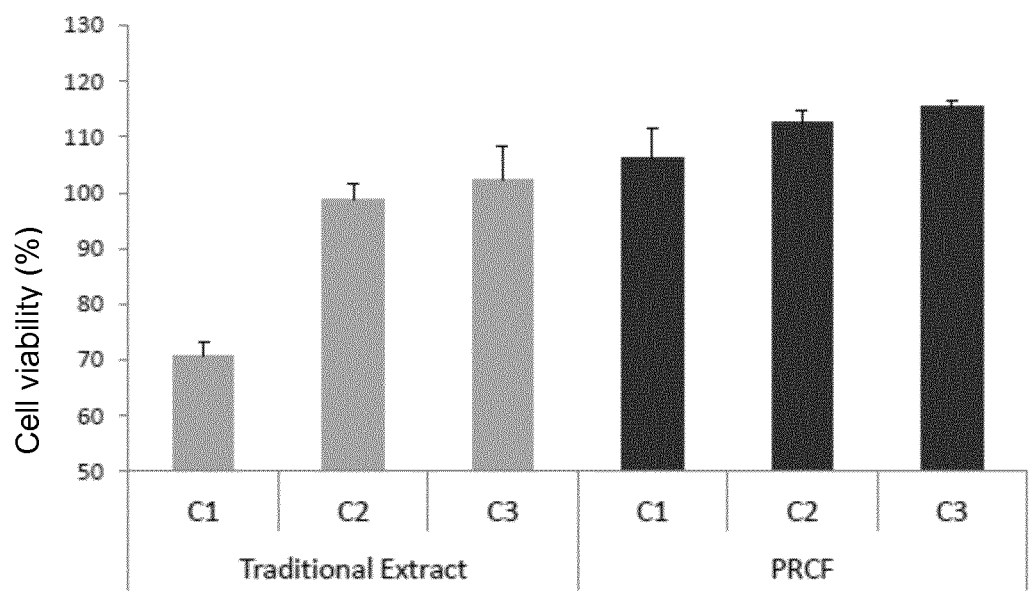

FIG. 2 demonstrates that PRCF promoted reversion of senescence at a greater extent than the extract in each tested concentration (C1 to C3). This also evokes the potential of cell lysates containing the cocktail of compounds useful in plant dedifferentiation/regeneration and active over animal cells. Safe applicability of these PCRF (cell lysates) over animal cells (HDF) can be seen in FIG. 5, wherein cell viability (% of living cells) in HDF (more than 20 passes) is shown. There are compared the extracts of *Daucus carota* (panel A) and *Punica granatum* (panel B) with the cell lysates of each specie (PRCF) at the same concentrations (C1 to C3; C1 (0.0019 µg/ml) C2 (0.00375 µg/ml) and C3 (0.0075 µg/ml)). PRCF were less toxic as the comparative extracts. In addition cell lysates promoting a cell viability over 100% may also be read as promoting a cell proliferative action.

Next, there were tested the cell-free supernatants (lyophilized conditioned media) of *Daucus carota* and *Punica granatum* obtained as above disclose in 1.1, and the SPE fractions from 1.2. In order to test the ability of promoting re-youth in senescent fibroblasts peroxiredoxin 4 and PARP were analysed (ELISA assays).

Figure 3:
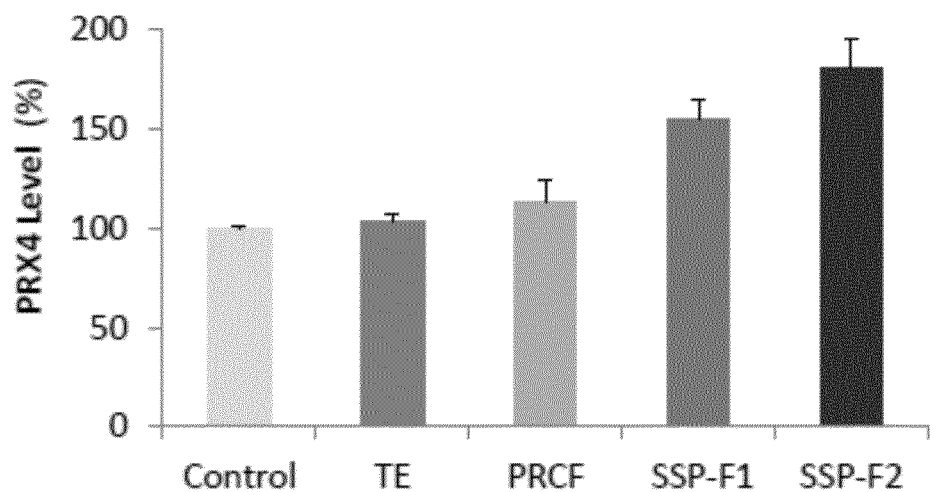
FIG. 3 shows also de peroxiredoxin 4 levels in HDF after the treatment with several compositions from *Daucus carota* (panel A) and from *Punica granatum* (Panel B). Also the levels of Poly [ADP-ribose] polymerase 1 (PARP-1) are depicted from *Daucus carota* (panel C) and from *Punica granatum* (Panel D). TE is a traditional extract of the plant, the control was the PRX4 in the senescent fibroblasts (considered as the 100%), PRCF corresponds to a cell lysate in glycerine in case of *Daucus carota*, and to a dried cell lysate in case of *Punica granatum*. SSPF1 corresponds to a lyophilized cell-free supernatant of each plant, and SSP-F2 corresponds to the SPE fraction comprising peptides with a molecular weight equal or lower than 30 kDa. PM (from pure molecule) is ellagic acid (positive control). PAPR1 is another marker serving for testing of senescence reversion in HDF, since it is an enzyme involved in repair of single-stranded DNA (ssDNA) breaks and is considered involved in DNA damage aging).
Figure 3:
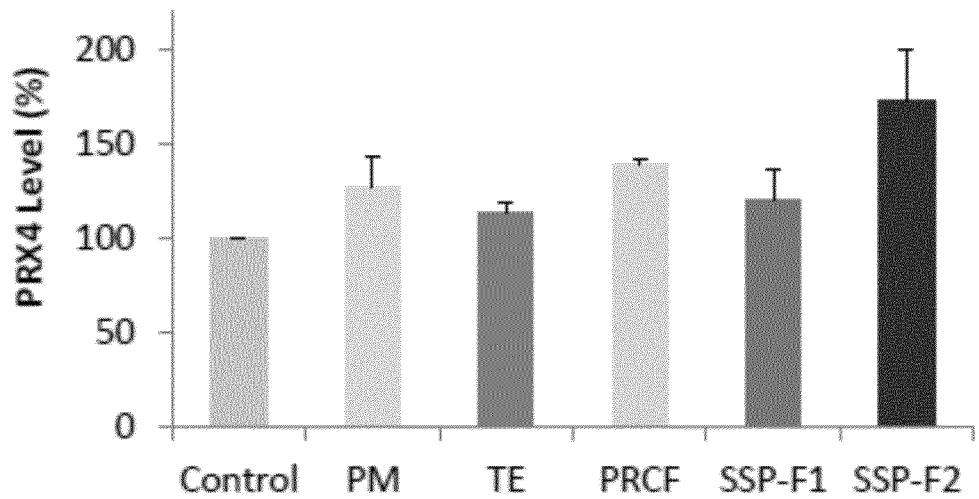

FIG. 3 shows the levels of PRX4 (panels A and B) and of PARP (panels C and D) observed in the fibroblast cultures after treatment (as above disclosed) with the cell-free supernatants (SSP-F1) and fractions (SSP-F2) of *Daucus carota* and *Punica granatum* prepared in 1.1 and 1.2. They are in addition compared with cell lysates of each plant (PRCF in each graphic A to C) and with an extract of each of the plant species.

The data clearly show that peptide fractions, obtained by SPE from the cell-free supernatants, attained the best senescence reversion (re-youth effect). All tested samples were comparable in terms of concentration of the active compounds contained by them. In addition, the data from the cell-free supernatants (the lyophilized cell-free supernatants, SSP-F1) gave rise to effects comparable or higher than those of the cell lysates (PRCF), but lower toxicity problems due to the lesser complexity of the mixture.

These are really interesting data, since they demonstrate firstly that senescent reversion of old skin cells can be achieved with the cell-free supernatants (conditioned media) that supported growing of plant cell suspension cultures. Secondly, this effect can be enhanced by purification of the peptide plant growth factors and/or plant transcription factors and/or epigenetic factors contained in these cell-free supernatants. It is to be noted that with the processing of the cell-free supernatants from liquid to lyophylization-resuspension and/or to peptide recovering by chromatography (in particular SPE), said cell-free supernatants or any peptides comprised therein are concentrated from 10 to 500 times. Therefore, they suppose less complex compositions, highly effective and obtainable with high yields by means of environmentally friendly process, at the time expensive cost associated to traditional extraction processes are avoided. In addition, use of these cell-free supernatants and fractions thereof imply re-valorisation of a part of the plant cell suspension cultures usually discarded.

Figure 4:
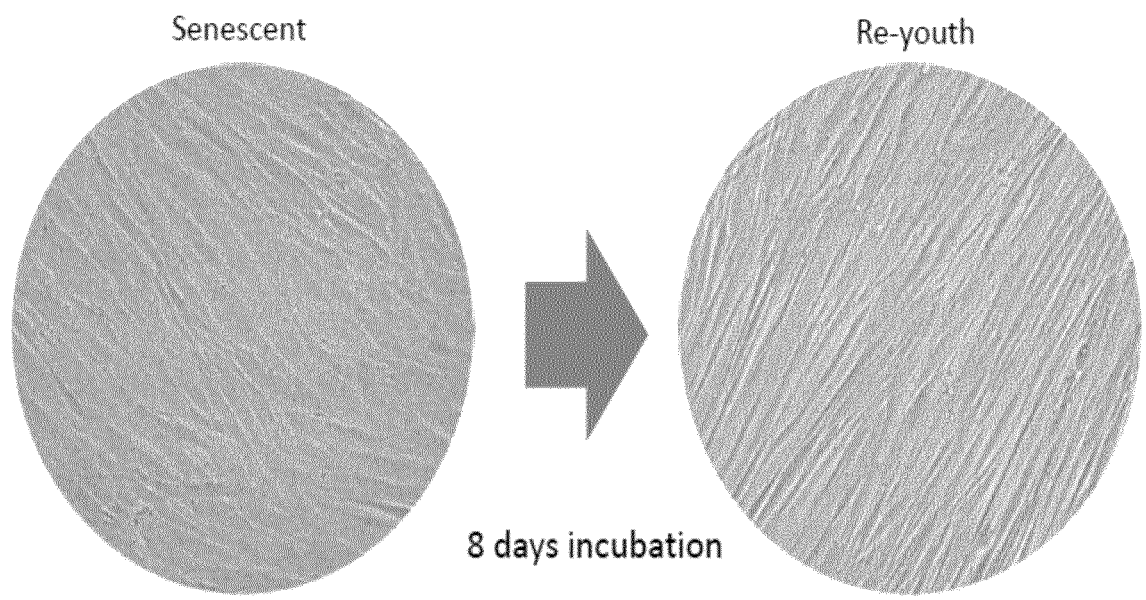
FIG. 4 is picture of a culture of old HDF (as disclose above, more than 20 passes) took before and after being treated for 8 days with a lyophilized cell-free supernatant of a *Centella asiatica* cell suspension culture.

Further and in order to illustrate macroscopically the effects of the cell-free supernatants of plant cell cultures, and of fractions thereof, both comprising peptides from 4 to 300 amino acids length, FIG. 4 shows a picture of a culture of old HDF (as disclose above) took before and after being treated for 8 days with a lyophilized cell-free supernatant of a *Centella asiatica* cell suspension culture, obtained as disclosed in 1.1.

The picture illustrates that the senescent phenotype, characterized by lower fibroblasts and extracellular matrix structuration and round-shaped cells rather than scattered cells, is reverted with only 8 days to a young phenotype, characterized by a greater cell density and extracellular matrix organization, as well as scattered-shaped morphology of cells).

All these data allow concluding that cell-free supernatants and fractions thereof enriched with peptides from 4 to 300 amino acids length or from 5 to 300 amino acids length, are effective active compositions for use in the treatment of skin conditions involving old skin cells (for example in photoaged skin or in premature skin aging).

Example 2

Additional Test of Cell-Free Supernatants and of Fractions Thereof Over a Model of Old Skin (Human Derman Fibroblasts of More than 20 Passes in Dulbeccos's; Replicative Senescence).

Following the same scheme as in Example 1 (1.3), the levels of Ki67 protein and of Senescence-associated beta-galactosidase (Sen-β-Gal) were determined on the model of senescent HDF of Example 1.3. The tested products were the above mentioned traditional extracts of *Punica granatum* and of *Daucus carota*; the cell lysates of each of the plants (also named PRCF in this description); the cell-free supernatants (SSP-F1, or conditioned medias) and the fractions (SSP-F2) comprising the peptides and obtained as disclosed in Example 1.2. Ellagic acid was the positive control (PM; from pure molecule); and the control or reference values were the Ki67 protein and Sen-β-Gal levels in the senescent fibroblasts (considered as the 100% for Ki67 and 0% in β-Gal).

Ki67 protein is decreased in senescent cells, while Sen-β-Gal is increased. Thus, if Ki67 protein levels are elevated due to the cell-free supernatants (SSP-F1, or conditioned medias) and the fractions (SSP-F2), this means that they promote re-youth. On the contrary, if Sen-β-Gal is decreased in relation to a control due to the cell-free supernatants (SSP-F1, or conditioned medias) and the fractions (SSP-F2), this means that they promote re-youth of the cells.

Ki67 protein levels were measured by an ELISA test ((Human KI-67 Protein ELISA Kit, YH Biosearch Laboratories, Ref. YHB1799HU-96T), as well as the levels of Sen-β-Gal with ELISA ((Human GLB (Galactosidase Beta) Elisa Kit, Elabscience, Ref. E-EL-H0991 for the levels; and Senescence Detection Kit, Abcam, Ref.ab6535 for cytochemistry analysis in cultures and microscope analysis).

Figure 6:
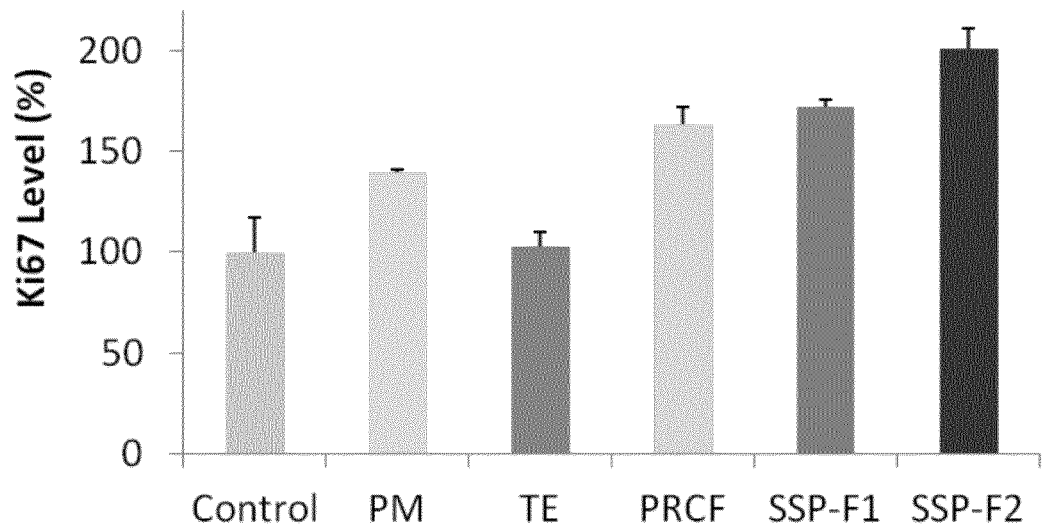
FIG. 6, related with Example 2, is a graph of bars showing expression of the Ki67 protein (Ki67 Level (%) in Y-axis) in human dermal fibroblasts (HDF) treated with several compositions from *Punica granatum* (Panel A), and from *Daucus carota* (panel B). Ellagic acid was the positive control (PM; from pure molecule); PRCF are cell lysates of each of the plants; TE is a traditional extract of each of the plants; SSP-F1 are the cell-free supernatants; SSP-F2 are fractions of the cell-free supernatants comprising peptides with a molecular weight equal or lower than 30 kDa; Control or reference values were the Ki67 protein in the non-treated senescent fibroblasts (considered as the 100%).
Figure 6:
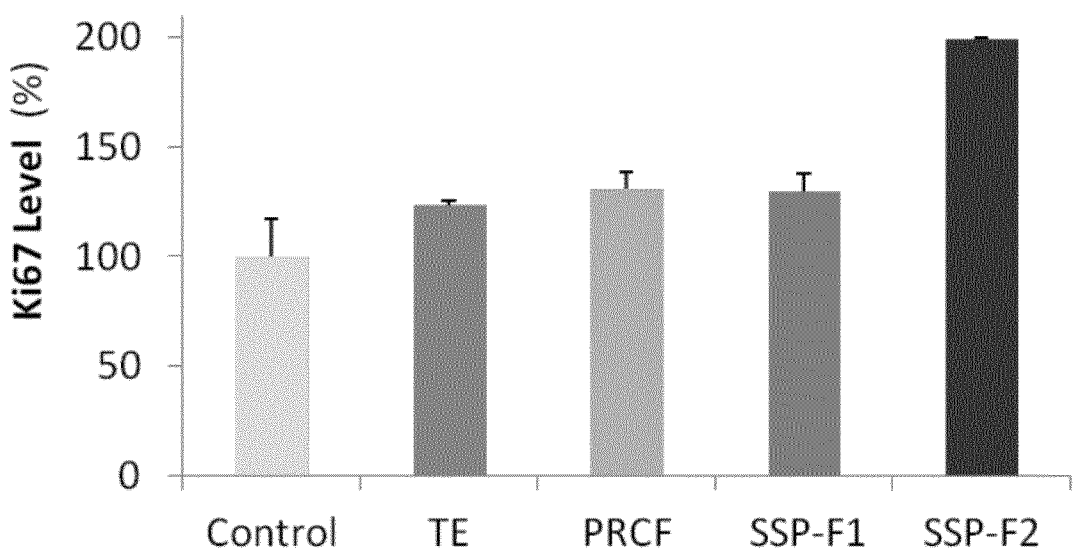
Figure 7:
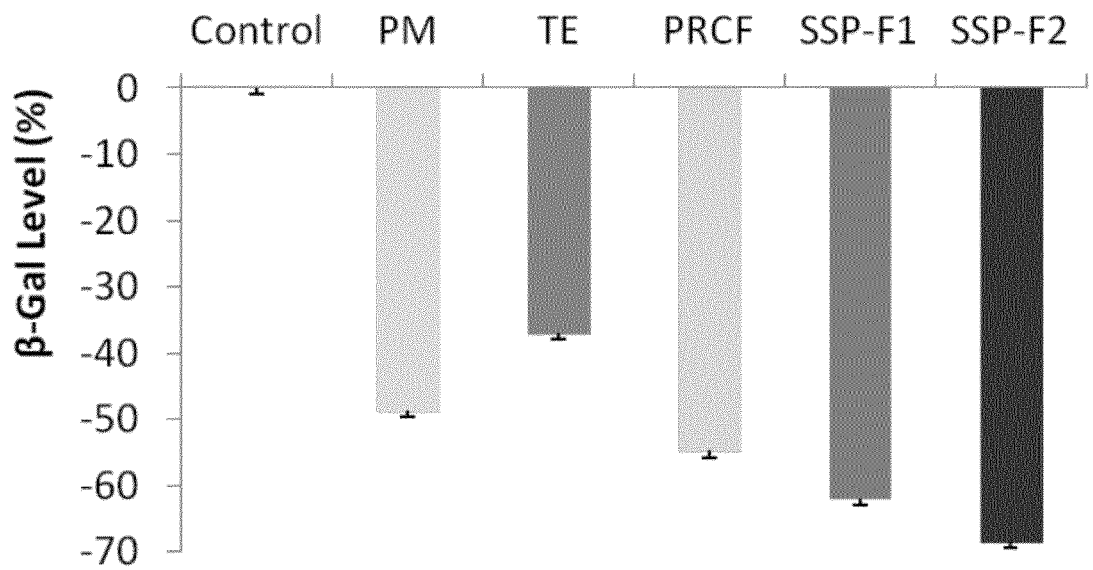
FIG. 7, also related with Example 2, is a graph of bars showing expression of the Sen-β-Gal levels (β-Gal Level (%) in Y-axis) in human dermal fibroblasts (HDF) treated with several compositions from *Punica granatum* (Panel A), and from *Daucus carota* (panel B). Ellagic acid was the positive control (PM; from pure molecule); PRCF are cell lysates of each of the plants; TE is a traditional extract of each of the plants; SSP-F1 are the cell-free supernatants; SSP-F2 are fractions of the cell-free supernatants comprising peptides with a molecular weight equal or lower than 30 kDa; Control or reference values were the Sen-β-Gal levels in the non-treated senescent fibroblasts (considered as the 0% after normalization).
Figure 7:
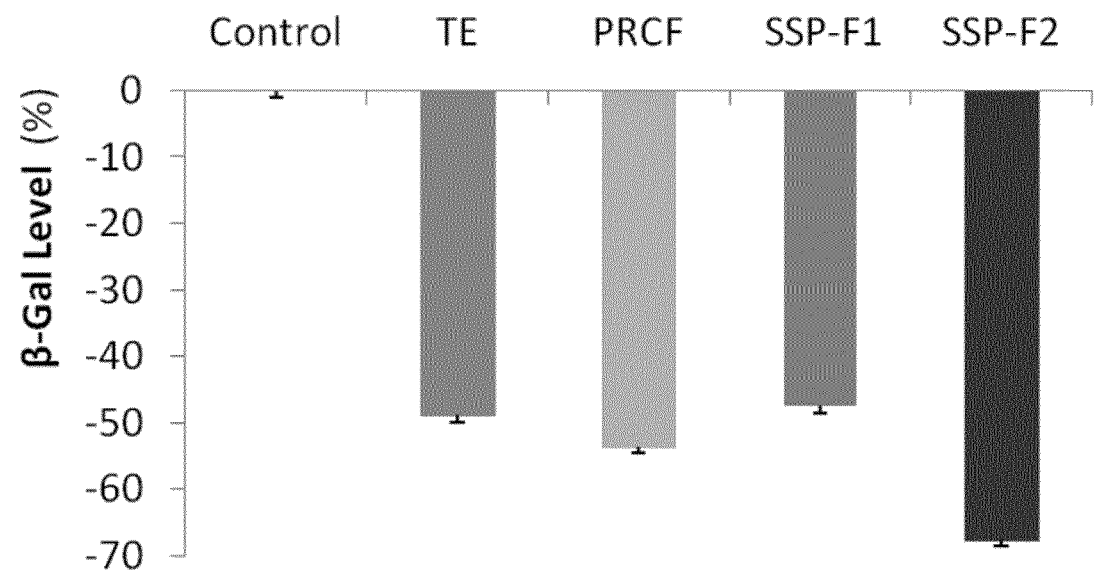

Results are depicted in FIG. 6 (Ki67 levels) and FIG. 7 (Sen-β-Gal levels). FIG. 6(A) depicts data from *Punica granatum*, FIG. 6(B) from *Daucus carota*. FIG. 7(A) depicts data from *Punica granatum*, FIG. 7(B) from *Daucus carota*.

In both species the cell-free supernatants (SSP-F1) and the fractions (SSP-F2) comprising the peptides promoted re-youth of senescent fibroblasts, as derived from the levels of each marker in comparison with the control references. In particular the fractions (SSP-F2) promoted re-youth at a higher and meaningful level than the traditional extracts tested.

Example 3

Assay of Proliferation of Human Fibroblasts of Hair Follicle Dermal Papilla Cells (HFDPC)

Further, a proliferation assay was conducted onto human hair follicle papilla cells (CELL APPLICATIONS, INC; Normal human hair follicles from temporal scalp. Single donor: 54 years old caucasian male; Ref. 602-05a. Lot. 2092.).

Next Table 2 shows tested material and controls:

| Assayed samples |
| --- |
| Basal control: non-treated cells maintained in culture media |
| Positive control cells treated with fibroblast growing factor (FGF) |
| Positive control cells treated with vascular endothelial growing factor (VEGF) |
| Minoxidil ((≥99% (TLC)), SIGMA, Ref. M4145. Stock solution: 16.67 mg/ml in Ethanol (25 mg Minoxidil + 1.5 ml Ethanol). |
| *Centella asiatica* (CA) 3.0 µg/ml C1 and 6.0 µg/ml C2 |
| *Curcuma longa* (CL): 3.0 µg/ml C1 and 6.0 µg/ml C2 |
| *Daucus carota* (DC): 1.6 µg/ml C1 and 1.5 µg/ml C2 (at 48 h) |
| *Vitis vinifera* (VV): 6.3 µg/ml C1 and 12.5 µg/ml C2 |
| *Sarcocapnos crassifolia* (SC): 12.5 µg/ml C1 and 25.0 µg/ml C2 |
| *Morinda citrifolia* (MC): 3.1 µg/ml C1 and 6.0 µg/ml C2 |
| *Olea europaea* (OE): 25.0 µg/ml C1 and 50.0 µg/ml C2 |
| *Lithops* sp. (LP): 3.0 µg/ml C1 and 1.5 µg/ml C2 |

The culture media was a Papilla Cell Basal Medium supplemented with the Growth Supplements kit (Relative composition: Fetal bovine serum, growth factors and antibiotics. Application: 6% v/v).

The cell-free supernatants (also labelled as Pre-pre-LyoP3) were obtained in particular as follows:

Culture supernatant obtained for all species as indicated in Example 1.1 for *Daucus carota*, *Punica granatum* and *Centella asiatica*, was centrifugated at 4600 rpm or 30 min at 4° C. A TFF (Tangential Flow Filtration) was done in the resulting product. The process comprised; a flux step, an equilibration, a filtration, a diafiltration and a final sanitization step. During the process, 2.5 l of PBS, 2.5 l of 20% Ethanol and NaOh 1N were used. After that a Reverse phase purification (RP) was done. (Oligo purification). The purification included 9 steps: addition of 5 Column volume (CV) water trifluoroacetic acid (TFA) 0.1%, addition of 5 CV CAN TFA 0.1%, inclusion of 5 CV water TFA 0.1% and the addition of TFA to achieve 0.1%. Then the sample was loaded, collected and washed with a 1 CV water TFA 0.1%. The elution was fractionated in 25-50-5-100% CAN with TFA 0.1%. The product was evaporated and resuspended in RP A. At the end of this purification pre-conditioned media 2 (pre cell-free supernatant) was obtained. This pre-conditioned media 2 was purified using a CEX (Cation exchange chromatography) and a AEX (Emphaze hybrid purifier). The process comprised 16 steps; addition of 5CV CEX A (sodium acetate 50 mM pH 4.5), 5 CV CEX B (Sodium acetate 50 mM NaCl 1M pH 4.5) and 5CV CEX A. A dilution 1:5 and a pH adjust to 4.5 with CEX A was also done such a sample loading, a collection of the sample, a washing with 1 CV CEX A and a fractioned elution with CEX B at 125 mM-250 mM-500 mM-1M. The elution received: 5 CV AEX A (Glycine 50 mM pH 9), 5 CV AEX B (Glycine 50 mM NaCl 1M at a pH 9) and 5 CV AEX A. A dilution 1:5 in AEX A and an adjust to pH 9 was done, as well as a sample loading, a collection of the sample, a washing with 1 CV AEX A and a fractioned elution with AEX B at 125 mM-250 mM-500 mM-1M. A final cell-free suspension (labeled Pre- pre-LyoP 3) was obtained. It was then lyophilized and resuspended for use at the desired concentrations.

Proliferation was assessed determining the proliferation index (%). Cell DNA replication was quantified by means of incorporated bromodeoxiuridine (BrdU) into DNA of treated cells. BrdU assay allows measuring cell proliferation based on cell capability of incorporating BrdU during S-phase of the cell cycle. Cells being divided incorporated BrdU that is further detected by means of antibodies and immunocytochemistry detection.

Cells were seeded at confluence in a 96-well plate. After stabilization and synchronization of cell cultures the tested products were added (at the final concentration indicated in Table 2. After that, BrdU was added to cultures and HFDPC were incubated at 37° C. until complete BrdU incorporation. BrdU amounts were proportional to the number of cell divisions and thus to the growth of the treated culture.

Figure 8:
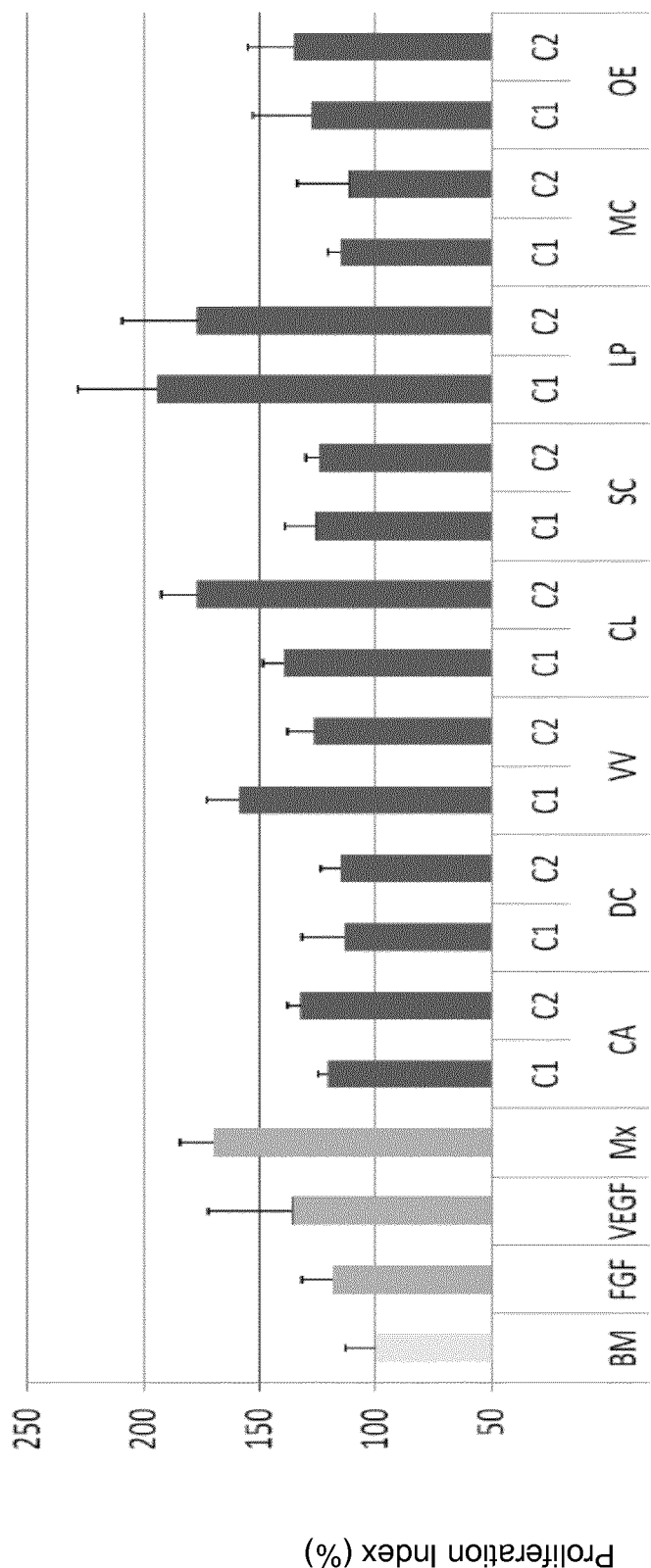
FIG. 8, related with Example 3 is graph with the proliferation index (%) of hair follicle dermal papilla cells (HFDPC), when treated with several compositions. Ctrl BM means basal control (non-treated HFDPC), which is accorded a 100% value of proliferation index; FGF means fibroblast growing factor, VEGF means vascular endothelial growing factor, C1 and C2 correspond to different concentrations of each of the cell-free supernatants of the tested species, as indicated in Table 2. Plant species names have been abbreviated also as indicated in Table 2. In Y-axis the proliferation index in percentage (%).

Data are depicted in FIG. 8, wherein it is shown the proliferation index (%) of HFDPC, calculated as the percentage of growing in relation to the basal control (non-treated HFDPC) which is accorded a 100% value of proliferation index.

As can be seen in FIG. 8, cell-free supernatants of the invention promoted cell proliferation taking as reference or basal control the non-treated cells cultured with media. For some species, the cell-free supernatants comprising the peptides with a molecular weight equal or lower than 30 kDa the proliferation index was much higher even than positive controls. If not, proliferation index was of the same order than the positive controls.

Minoxidil data were added, since this compound is usually employed as hair-loss treatment involved on proliferation of hair follicle dermal papilla. It is to be noted that some of the cell-free supernatants had an effect comparable to minoxidil.

Example 4

In Vivo Re-Youth (Anti-Aging) Assay

A conditioned media of *Centella asiatica* obtained as exposed in Example 1 and formulated as indicated below (Table 3) was tested in vivo in order to determine if it could also promote a re-youth effect (or anti-aging effect) in real skin.

TABLE 3

Tested compounds: Placebo and a cream comprising from 0.5-5.0% (w/w) of *Centella asiatica* cell-free suspension culture prepared as in Example 1 and previously diluted (½) in glycerine. Next Table 3 shows qualitative compositions.

Placebo (white cream, pH = 6.34, viscosity (cP): 21760)
Glyceryl stearate/PEG-100 stearate, Cetearyl alcohol, Isohexadecane, middle-chain triglycerides, Glycerin, Disodium EDTA, Aqua, Sodium Polyacrylate (and) Hydrogenated
Polydecene (and) Trideceth-6, Benzyl Alcohol & Salicylic Acid & Glycerin & Sorbic Acid
*Centella asiatica* cream (CA) (white cream, pH = 6.32, viscosity (cP): 23800)
Glyceryl stearate/PEG-100 stearate, Cetearyl alcohol, Isohexadecane, middle-chain triglycerides, Glycerin, Disodium EDTA, Aqua, Sodium Polyacrylate (and) Hydrogenated
Polydecene (and) Trideceth-6, Benzyl Alcohol & Salicylic Acid & Glycerin & Sorbic Acid, and *Centella asiatica* cell-free suspension culture prepared as in Example 1 and previously diluted (½) in glycerine.

With this aim 40 female volunteers (>50 years old) were recruited and previously characterized of presence of photo-damages. The effectivity of the product was determined in terms of anti-wrinkle and anti-puffiness treatment using objective analysis via VISIA by image analysis and clinical efficacy and perceived efficacy. VISIA quantified parameters were: spots, wrinkles, texture, pores, UV spots, brown spots, red areas and porphyrins.

TABLE 4

| VISIA details | |
| --- | --- |
| Equipment: | VISIA CR |
| Serial number: | 930567 |
| Model: | Visiav531 |
| Manufacturer: | Canfield Imaging Systems |
| Software | Visiav531 - Version: v5.3.3 2011 - 1208a | photographs representing the t=0 were taken with a digital image. For the test half part of face was treated and onto the other half placebo was administered. Regions in the eye area were demarcated, and they were held as controls over the treatment according to the number of applications of the test product.

Images were taken at day 28 after initial of treatment and at day 56 after initial of treatment.

Besides, 20 volunteers (20-25 years old) were used only for t=0 as reference group.

Statistical treatment of results was accomplished with Prism 4.0 software using Tukey method.

In all volunteers (>50 years old) all studies VISIA and Cutometer parameters were improved by resembling youth skin In relation to cutometer (determining deformation of skin vs. time), there were determined the following parameters:

Ue parameter (skin firmness); a reduction of the parameter indicates an increase in skin firmness CF parameter (skin firmness coefficient); CFti=Ue(t0)/Ue(ti); wherein t is time of test Skin elasticity parameter (Ur/Uf; wherein Ur is the immediate retraction and Uf is the total skin deformation); and increase in Ur/Uf indicates an increase in skin elasticity.

Skin elasticity coefficient (CE); CEti=(Ur/Uf)ti/(Ur/Uf)t0

Next Table 5 shows the results obtained with the placebo and the tested compound:

TABLE 5

| | Cutometer results | | | | | | | |
| --- | --- | --- | --- | --- | --- | --- | --- | --- |
| | T28 d | | | | T56 d | | | |
| | Ue | CF | Ur/Uf 28-0 | CE | Ue | CF | Ur/Uf 56-0 | CE |
| Placebo | n.s. p > 0.05 | n.s. p > 0.05 | n.s. p > 0.05 | n.s. p > 0.05 | 6.40% s.s. p < 0.05 | s.s. p < 0.05 | n.s. p > 0.05 | s.s. p < 0.05 |
| CA | 15.9% s.s. p < 0.05 | | 6.8% s.s. p < 0.05 | | 18.8% s.s. p < 0.005 | | 7.8% s.s. p < 0.05 | |

There were also studied (as clinical effectiveness and perceived effectiveness) the following parameters: skin-smoothness, skin luminosity, "more radiant skin", skin renewed, skin with fewer wrinkles, skin completely smooth, swelling reduction (anti-puffiness).

Biometric measurements were also made in each site using Cutometer MPA 580 instrument with a probe with a 2-mm opening (CKelectronic, Germany) to assess skin firmness and elasticity at each time. Each measurement was made with 10 cycles of 3 seconds of suction followed by 3 seconds of relaxation with pressure of 200 mbar.

The volunteers were required not to use any moisturizer or cosmetic preparation in the areas of the skin to be studies at least 24 hours before the test. They were first conditioned for 30 minutes at room test for baseline assessments and

*Centella asiatica* cream improved in a meaningful way results at initial of the test:

Ue parameter (skin firmness): Ue was reduced in 15.9% at 28 days and a 18.8% at 56 days; increasing skin firmness of the face in 86.4% and 90% of the volunteers, at 28 and 56 days, respectively.

Skin elasticity: Ur/Uf, increased 6.8% at 28 days, and 7.8% at 56 days; increasing elasticity of the face in 81.8% and 86.4%, of the volunteers, at 28 and 56 days, respectivaly.

Thus, *Centella asiatica* cream increased skin firmness and elasticity at 28 and 56 days, in relation to t=0. At 56 days the differences progressively increased and were meaningful in relation to placebo.

Example 5

Wound Healing Test (or Scratch Test) with Fractions of Conditioned Media (CM) Comprising Peptides from 5 to 300 Amino Acids (3-30 KDa Aprox) Length on Human Gingival Fibroblast (HGF).

Human gingival fibroblasts were seeded in a 24-well plate and were grown to confluence. A 2 mm width scratch was done on the culture monolayer. Then the test products in culture medium were added and the cicatrisation process was followed by means of phase contrast microscopy. With this aim, photographs were taken at initial of the test (T=0 h) before the scratching and after the treatment (at 12 h and at 72 h). Cicatrisation process was evaluated by quantifying wound area reduction at each time.

Next Table 6 shows features of tested products and of controls:

TABLE 6

Samples assayed in wound healing test
Assayed samples

Basal control (BC) 0.1% Fetal bovine serum (FBS)
Positive control (Ctrl+)10% (FBS)
Positive control (Ctrl+) tissular growing factor-β1 (TGF-β1)
*Centella asiatica* (CA) fractions: 0.05 µg/ml of 30 kDa fraction and 3 kDa fraction
*Curcuma longa* (CL) fractions: 0.03 µg/ml of 30 kDa fraction and 3 kDa fraction
*Daucus carota* (DC) 0.1 µg/ml of 30 kDa fraction and 0.07 µg/ml of 3 kDa fraction
*Vitis vinifera* (VV): 0.1 µg/ml of 30 kDa fraction and 3 kDa fraction
*Sarcocapnos crassifolia* (SC): 0.1 µg/ml of 30 kDa fraction and 0.01 µg/ml of 3 kDa fraction
*Olea europaea* (OE): 0.05 µg/ml of 30 kDa fraction and 3 kDa fraction
*Lithops* sp (LP).: 0.052 µg/ml of 30 kDa fraction and 0.03 µg/ml of 3 kDa fraction
Peptide 4Aa (SEQ ID NO: 1): 5 µg/ml and 0.05 µg/ml
Peptide 4AaS1 (SEQ ID NO: 2): 5 µg/ml and 0.05 µg/ml
Peptide 4AaS2 (SEQ ID NO: 3): 5 µg/ml and 0.05 µg/ml Obtention of fractions of the cell-free plant cell culture supernatants was performed as indicated for Example 1 (1.2). Particular separation of a fraction comprising the peptides from 0 to 3 KDa and from 0 to 30 kDa was achieved in particular, as detailed below:

Culture supernatant of all species obtained as indicated in Example 1.1 for *Daucus carota, Punica granatum* and *Centella asiatica*, was centrifugated at 4600 rpm or 30 min at 4° C. A TFF (Tangential Flow Filtration) was done in the resulting product. The process comprised; a flux step, an equilibration, a filtration, a diafiltration and a final sanitization step. During the process, 2.5 l of PBS, 2.5 l of 20% Ethanol and NaOh 1N were used. After that a Reverse phase purification (RP) and final filtration were performed. For RP the purification included 9 steps: addition of 5 Column volume (CV) water trifluoroacetic acid (TFA) 0.1%, addition of 5 CV CAN TFA 0.1%, inclusion of 5 CV water TFA 0.1% and the addition of TFA to achieve 0.1%. Then the sample was loaded in RP A, it was eluted elution in 100% CAN and the final step was a resuspension in saline buffer. The final filtration was done with a 3 kDa o 30 kDa Amicro Ultra filter.

Materials

RP A: Water TFA 0.1%
RP B: CAN TFA 0.1%
CEX A: Sodium acetate 50 mM pH 4.5
CEX B: Sodium acetate 50 mM pH 4.5
AEX A: Glycine 50 mM pH 9
AEX B: Glycine 50 mM NaCl 1M pH 9

Peptides tested corresponded to $CH_3$—C(O)—YIYT-$NH_2$ (SEQ ID NO: 1); $CH_3$—C(O)-$Xaa_1$IYT-$NH_2$ wherein $Xaa_1$ is a sulphated Y (sulphate group, $SO_3H$) (SEQ ID NO: 2); and $CH_3$—C(O)-YI$Xaa_2$T-$NH_2$ wherein $Xaa_1$ is a sulphated Y (SEQ ID NO: 3). They are synthetic peptides miming the 4 amino acid peptide named phytosulfokine-β (PSK-β), isolated from conditioned media of plant cells in suspension (see Matsubayashi et al., "Phytosulfokine, sulphated peptides that induce the proliferation of single mesophyll cells of Asparagus officinalis L.", *Proc. Natl. Acad. Sci.*—1996, vol. no. 93, pp.: 7623-7627).

Assayed peptide sequences were assembled by solid phase methods using a Fmoc-based protection scheme on a Rink amide resin. The side chain of the Tyr (Y) residues was protected with a t-butyl group. Deprotection of the N-terminal Fluorenylmethyloxycarbonyl chloride (Fmoc) groups was done with 20% piperidine in dimethylformamide (DMF) in 5 min. Synthesis was performed in a Prelude automated synthesizer (Protein Technologies, Tucson, AZ, USA). After chain assembly, the peptide-resin was treated with 90% trifluoroacetic acid-5% triisopropylsilane-5% water for 1 h, the corresponding filtrate was treated with 3 volumes of chilled ethyl ether to precipitate the peptide. After centrifugation, the supernatant was carefully removed and he pellet (containing the peptides) were redissolved in aqueous (5% v/v) acetic acid and lyophilized. Purification of the crude product was done by preparative reverse-phase HPLC using water/acetonitrile gradients (both with 0.05% trifluoroacetic acid). The purified peptides were homogeneous (>95%) by HPLC and had the expected molecular mass by electrospray mass spectrometry.

Figure 9A:
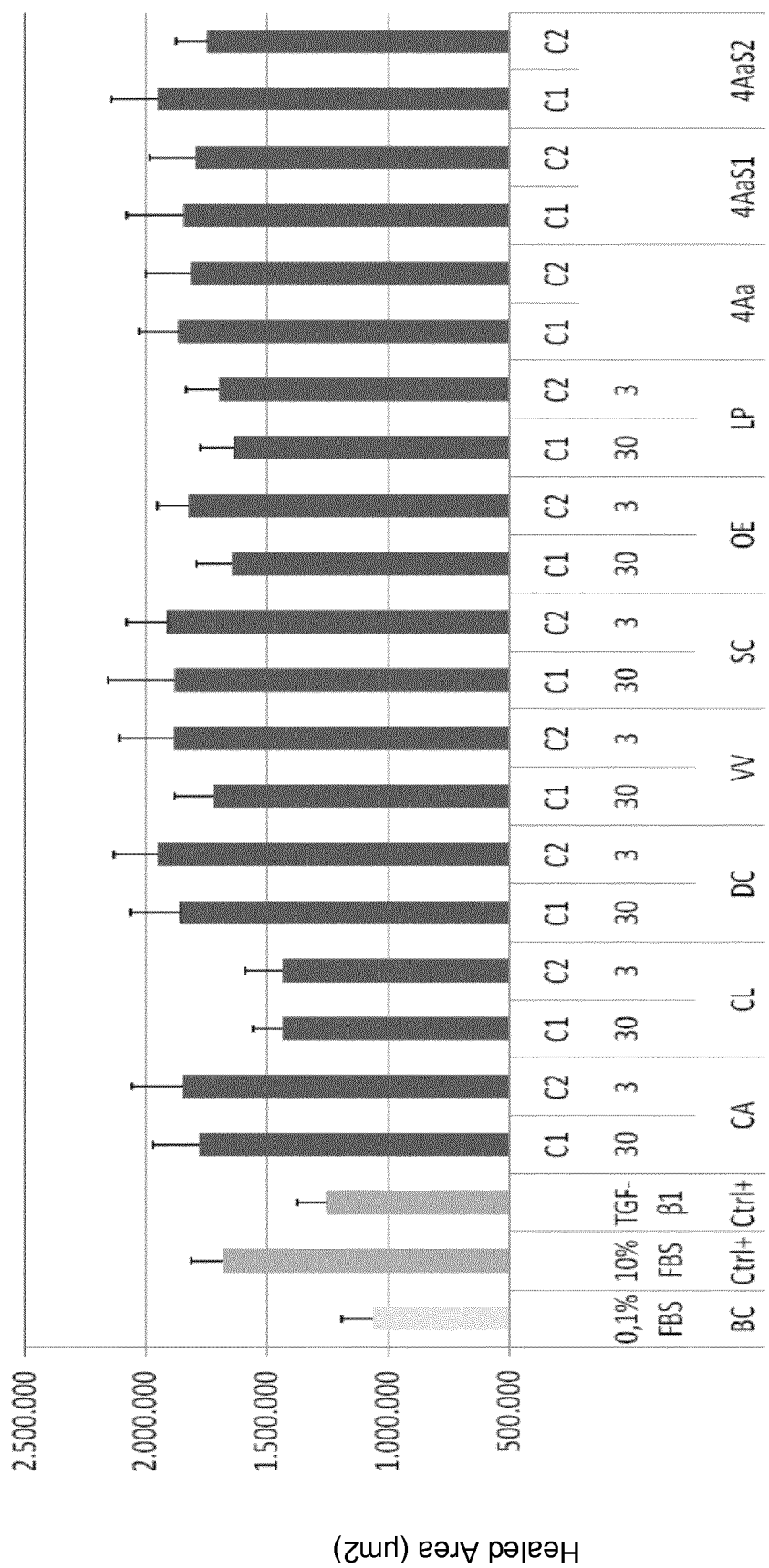
FIG. 9, related to Example 5, shows in (A) the Healed Area (in µm2) of several compositions, and in (B) the percentage of wound healing increase relation to the basal control after 48 h of treatment. BC means basal control; Crtl+ are positive controls (in particular Fetal bovine serum (FBS) and tissular growing factor-β1 (TGF-β1)), C1 and C2 correspond to different concentrations of each of the cell-free supernatant fractions (3 KDa or 30 KDa filtered) of the tested species, as indicated in Table 6. Plant species names have been abbreviated also as indicated in Table 6. 4Aa, 4AaS1 and 4AaS2 are peptides of SEQ ID NO: 1, 2 and 3, respectively.
Figure 9B:
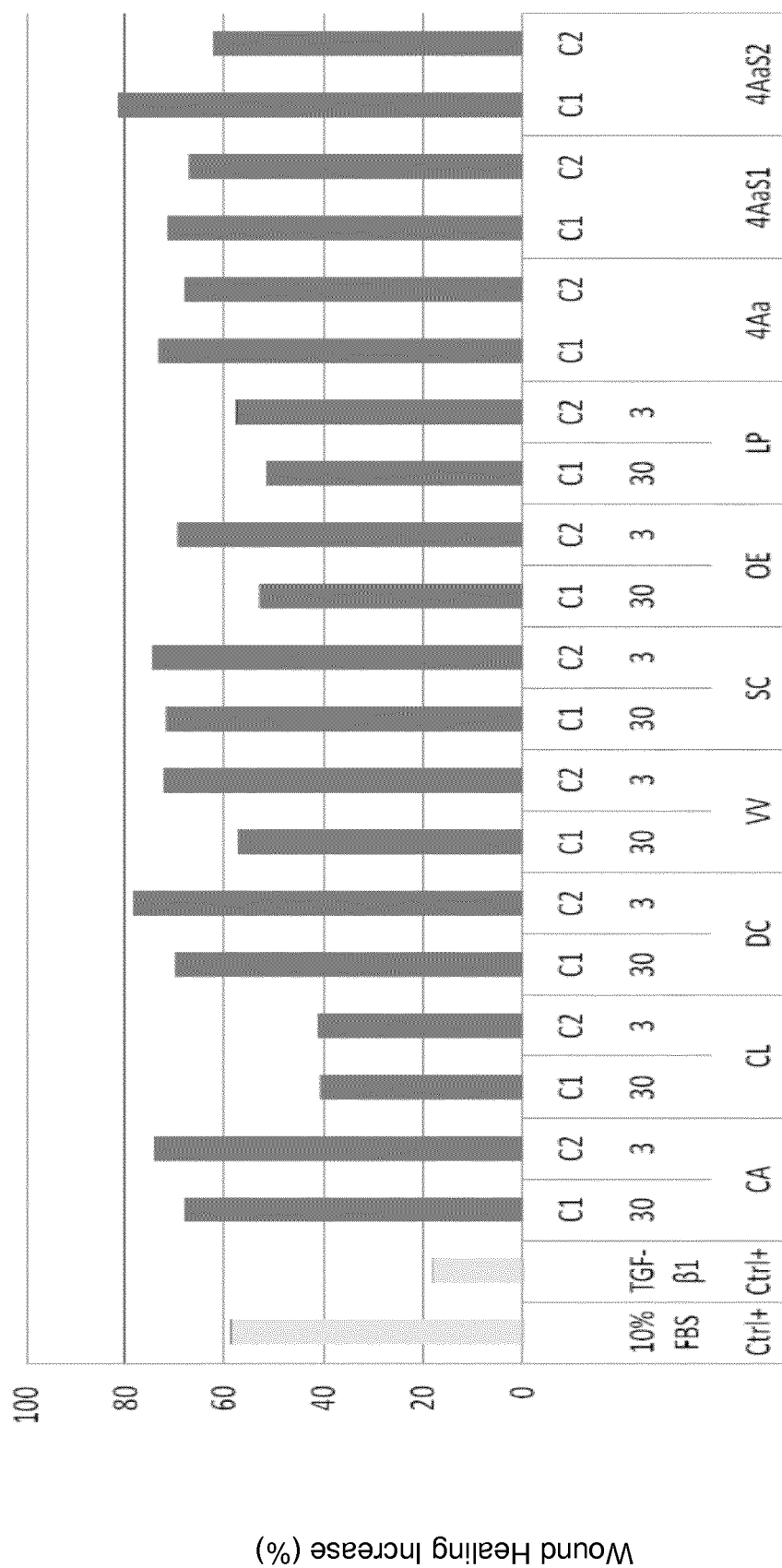

Data at the end of the test (5 days of treatment) are depicted in FIG. 9(A), wherein the wound healing potential is depicted as the Healed Area (in $\mu m^2$) for each tested fraction of the plants or for each assayed peptide. FIG. 9(B) it is depict the wound healing increase (in percentage %) in relation to the basal control after 48 h of treatment.

The results derive from a triplicate test. Values of cicatrised area (or % of cicatrisation) are the mean values.

From this FIG. 9 it is directly deduced that all tested fractions were more effective than the basal control and they provided effects similar to the positive controls or even higher. This data allow affirming that the fractions of the conditioned medias with the concentrated peptides of 3-30 kDa are real wound healing promoters. On the other side, the tested peptides also provided the desired effect, proving that the peptides itself contribute to the effect of the fractions.

For reasons of completeness, various aspects of the invention are set out in the following numbered clauses:

Clause 1. Cell-free supernatant that previously supported the growth of a dedifferentiated plant cell suspension culture, or a fraction of said cell-free supernatant for use as a medicament, wherein said cell-free supernatant or said fraction comprises peptides from 5 to 300 amino acids length, said peptides selected from peptide plant growth factors, plant transcription factors and mixtures thereof, and said cell-free supernatant or said fraction without having cytoplasmic cell contents from the cell lysis and membranes and/or cell walls.

Clause 2. The cell-free supernatant or fraction thereof for use according to clause 1, wherein the medicament is for use as cicatrisation skin agent, and/or for use as skin wound healing agent, and/or for use as skin re-youth agent.

Clause 3. The cell-free supernatant or fraction thereof for use according to any of clauses 1-2, wherein the dedifferentiated plant cell culture suspension is from a plant selected from the group consisting of *Daucus carota, Centella asiatica, Punica granatum, Gossypium herbaceum, Sarcocapnos crassifolia, Curcuma longa, Linum usitatissimum, Vitis vinifera, Lithops pseudotruncatella, Arnica montana, Morinda citrifolia, Symphytum officinale, Cannabis sativa, Olea europaea*, and *Camellia sinensis*.

Clause 4. The cell-free supernatant or fraction thereof for use according to any of clauses 1-3, wherein the supernatant, or a fraction of said cell-free supernatant comprises plant peptide growth factors, which are selected from the group consisting of Phytosulphokine-α (PSK-α), Plant Peptide Containing Sulphated Tyrosine-1 (PSY1), Rapid Alkalinization Factor (RALF), Tracheary Element Differentiation Inhibitory Factor (TDIF), Clavata-3 (CLV3), Clavata-Embryo Surrounding Region-Related (CLE), Tapetum Determinant-1 (TPD1), Epidermal Patterning Factor-1 (EPF1), Inflorescence Deficient in Abscission (IDA), Embryo Surrounding Region-Related (ESR), Polaris peptide (PLS), Root meristem Growth Factor (RGF), Egg Cell-Secreted Protein (EC1), C-terminally Encoded peptide (CEP), Early Nodulin 40 (ENOD40), Systemin, 5-locus Cystein Rich proteins (SCR), and mixtures thereof.

Clause 5. The cell-free supernatant or fraction thereof for use according to any of clauses 1-4, wherein the cell-free supernatant or fraction thereof is obtainable by a method comprising:
(a) growing dedifferentiated plant cells from a friable callus in a liquid nutrient culture medium from 5 to 15 days, to obtain a conditioned media supporting the growth of the dedifferentiated plant cells;
(b) removing entire plant cells from the conditioned media without lysing the cells, to obtain a cell-free supernatant comprising peptides from 5 to 300 amino acids length, said peptides selected from peptide plant growth factors, plant transcription factors and mixtures; and
(c) optionally carrying out a protein separation process by means of a separation technique selected from the group consisting of chromatography, filtration, ultrafiltration, protein precipitation, and combinations thereof, to obtain a fraction of the cell-free supernatant.

Clause 6. —The cell-free supernatant or fraction thereof for use according to clause 5, wherein the cell-free supernatant or fraction thereof is obtainable by a method comprising freeze-drying the cell-free supernatant after step (b) to obtain a freeze-dried supernatant.

Clause 7—The cell-free supernatant or fraction thereof for use according to clause 6, wherein the cell-free supernatant or fraction thereof is obtainable by further concentrating from 100 to 500 times the obtained freeze-dried cell-free supernatant.

Clause 8. The cell-free supernatant or fraction thereof for use according to any of clauses 1-7, wherein the dedifferentiated plant cell suspension culture is cultured at a cell density, expressed as number of cells per volume unit of suspension culture, from $1.10^5$ cell/ml of suspension culture to $1.10^7$ cell/ml suspension culture.

Clause 9. The cell-free supernatant or fraction thereof for use according to any of clauses 1-8, wherein the dedifferentiated plant cell suspension culture is submitted to stress conditions by means of elicitation processes.

Clause 10.—A fraction of a cell free-supernatant that previously supported the growth of a dedifferentiated plant cell suspension culture from a plant selected from the group consisting of *Daucus carota, Centella asiatica, Punica granatum, Gossypium herbaceum, Sarcocapnos crassifolia, Curcuma longa, Linurn usitatissimum, Vitis vinifera, Lithops pseudotruncatella, Arnica montana, Morinda citrifolia, Symphytum officinale, Cannabis sativa, Olea europaea*, and *Camellia sinensis*, said fraction:

comprising peptides from 5 to 300 amino acids length, said peptides selected from peptide plant growth factors, plant transcription factors and mixtures thereof, and the fraction without having cytoplasmic cell contents from the cell lysis and membranes and/or cell walls; and obtainable by a method comprising:
(a) growing the dedifferentiated plant cells from a friable callus in a liquid nutrient culture medium from 5 to 15 days, to obtain a conditioned media supporting the growth of the dedifferentiated plant cells;
(b) removing entire plant cells from the conditioned media without lysing the cells, to obtain a cell-free supernatant comprising peptides from 5 to 300 amino acids length; and
(c) carrying out a protein separation process by means of a separation technique selected from the group consisting of solid-phase extraction chromatography, size-exclusion chromatography, filtration, ultrafiltration, protein precipitation, and combinations thereof, to obtain a fraction of the cell-free supernatant.

Clause 11. The cell-free fraction according to clause 10, wherein step (c) is carried out by means of solid-phase extraction chromatography Clause 12. A skin topical composition which comprises an effective amount of a cell-free fraction of a supernatant of a dedifferentiated plant cell suspension culture as defined in any of clauses 10-11, together with one or more appropriate topical pharmaceutically or cosmetically acceptable excipients or carriers.

Clause 13. The skin topical composition according to clause 12, which comprises glycerine as at least one of the topical pharmaceutically or cosmetically acceptable excipients.

REFERENCES CITED IN THE APPLICATION

US2014072619
WO2012130783
EP2436759
Ryan et al., "Polypeptide Hormones", *The Plant Cell*—2002, S251-S264 Supplement
Czyzewicz et al., "Message in a bottle: small signalling peptide outputs during growth and development", Journal of Experimental Botany—2013, vol. no. 64(17), pp.: 5281-5296
Goberdhan et al., "A biomarker that identifies senescent human cells in culture and in aging skin in vivo", *Proc.Natl.Acad.Sci*—1995, Vol No. 92, pp.: 9363-9367
Matsubayashi et al., "Phytosulfokine, sulphated peptides that induce the proliferation of single mesophyll cells of Asparagus officinalis L.", *Proc. Natl. Acad. Sci.*—1996, vol. no. 93, pp.: 7623-7627

The invention claimed is:

1. A method for treating a skin wound in a human in need thereof comprising:
   administering to the human in need thereof a therapeutically effective amount of a cell-free supernatant or a cell-free supernatant fraction, wherein said cell-free supernatant or a cell-free supernatant fraction thereof is obtained by a method comprising:
   (i) growing dedifferentiated plant cells from a friable callus in a liquid nutrient culture medium for 5 days to 15 days, to obtain a conditioned media supporting the growth of the dedifferentiated plant cells; and
   (ii) removing the entire plant cells from the conditioned media without applying a lysing step to the cells, to obtain the cell-free supernatant or the cell-free supernatant fraction comprising peptides from 4 amino acids to 300 amino acids in length, said peptides being selected from the group consisting of peptide plant growth factors, plant transcription factors, epigenetic factors, and mixtures thereof;
   wherein the dedifferentiated plant cell culture suspension is from a plant selected from the group consisting of *Daucus carota, Centella asiatica, Punica granatum, Gossypium herbaceum, Sarcocapnos crassifolia, Curcuma longa, Linum usitatissimum, Vitis vinifera, Lithops pseudotruncatella, Morinda citrifolia, Syvmphytum officinale, Cannabis sativa, Olea europaea*, and *Camellia sinensis*.

2. The method of claim 1, wherein said cell-free supernatant or said cell-free supernatant fraction comprises peptides from 5 amino acids to 300 amino acids in length, said peptides selected from the group consisting of peptide plant growth factors, plant transcription factors, and mixtures thereof.

3. The method of claim 1, wherein the cell-free supernatant or the cell-free supernatant fraction thereof is obtained by a method comprising freeze-drying the cell-free supernatant or the cell-free supernatant of (ii) to obtain a freeze-dried supernatant or a freeze-dried cell-free supernatant fraction.

4. The method of claim 1, wherein the cell-free supernatant or the cell-free supernatant fraction thereof is obtained by further concentrating from 100 times to 500 times the obtained freeze-dried cell-free supernatant or the freeze-dried cell-free supernatant.

5. The method of claim 1, wherein the dedifferentiated plant cell suspension culture is cultured at a cell density, expressed as number of cells per volume unit of suspension culture, from $1\times10^5$ cell/ml of suspension culture to $1\times10^7$ cell/ml suspension culture.

6. The method of claim 1, wherein for the fraction of the cell-free supernatant, the method further comprises carrying out a protein separation process by means of a separation technique selected from the group consisting of chromatography, filtration, ultrafiltration, protein precipitation, and combinations thereof.

* * * * *